United States Patent [19]

Beckmann et al.

[11] Patent Number: 5,098,837

[45] Date of Patent: Mar. 24, 1992

[54] MACROLIDE BIOSYNTHETIC GENES FOR USE IN STREPTOMYCES AND OTHER ORGANISMS

[75] Inventors: Robert J. Beckmann, Indianapolis; Karen L. Cox, Martinsville; R. Nagaraja Rao, Indianapolis; Mark A. Richardson, Indianapolis; Eugene T. Seno, Indianpolis, all of Ind.

[73] Assignee: Eli Lilly and Company, Indianapolis, Ind.

[21] Appl. No.: 203,387

[22] Filed: Jun. 7, 1988

[51] Int. Cl.⁵ .................. C12N 1/21; C12N 15/09; C12N 15/76
[52] U.S. Cl. .................. 435/172.3; 435/71.2; 435/76; 435/91; 435/169; 435/172.1; 435/252.35; 435/320.1; 435/886; 536/27; 935/6; 935/9; 935/22; 935/29; 935/59; 935/60; 935/61; 935/66; 935/72; 935/75
[58] Field of Search .................. 435/69.1, 76.2, 91, 435/172.1, 172.3, 252.3, 252.35, 320.1, 76, 72, 71.3, 169, 886; 536/27; 935/6, 9, 22, 29, 33, 59, 60, 61, 66, 75

[56] References Cited

U.S. PATENT DOCUMENTS 4,713,337  12/1987  Jasin et al. .................. 435/172.3
4,753,880  6/1988   Schaus et al. ................ 435/172.3
4,935,340  6/1990   Baltz et al. .................. 435/6

FOREIGN PATENT DOCUMENTS 0204549  12/1986  European Pat. Off. .
0238324  9/1987   European Pat. Off. .

OTHER PUBLICATIONS

Anzai et al., 1988 (Feb.), *The Journal of Antibiotics* vol. 41(2):226–233.
Gutterson et al., 1983, *PNAS*, vol. 80:4894–4898.
Baltz and Seno, 1981, Antimicrobial Agents and Chemotherapy 20: 214–225.
Baltz et al., 1986, *In Protein Engineering*, 365–381 (Inouye and Sarma, eds., Academic Press, Inc.).
Lacroix et al., *Mutational Cloning in Streptomyces ambofaciens*, Abstract from the 208th Meeting of the Genetical Society of Great Britain, Apr. 14–15, 1988, held at the John Innes Institute.
Seifert et al., 1986, P.N.A.S. 83: 735–739.
Huisman et al., 1987, Genetics 116: 191–199.
Snyder et al., Proc. Natl. Acad. Sci. USA 83:730–734 (1986).
PCT Publication Ser. No. WO 88-01646, Published Mar. 10, 1988.

*Primary Examiner*—Richard C. Peet
*Attorney, Agent, or Firm*—Amy E. Hamilton; Leroy Whitaker

[57] ABSTRACT

Spiramycin antibiotic biosynthetic genes of *Streptomyces ambofaciens* are provided by the present invention, in addition to a variety of recombinant DNA vectors. The genes also function in other macrolide producing organisms. The genes can be used to increase or otherwise alter the macrolide antibiotic-producing ability of an organism. The present invention also provides host strains comprising mutant spiramycin biosynthetic genes which can be used to generate novel antibiotics. Also provided is a method for preparing the mutant gene comprising mutating cloned spiramycin biosynthetic DNA by transposon mutagenesis with subsequent transformation into a macrolide-antibiotic producing host and homologous recombination into its genome, to generate stable mutant cell lines.

43 Claims, 11 Drawing Sheets

MACROLIDE BIOSYNTHETIC GENES FOR USE IN STREPTOMYCES AND OTHER ORGANISMS

SUMMARY OF THE INVENTION

The present invention comprises novel macrolide antibiotic biosynthetic genes, the polypeptide product encoded by these genes, and a method for using said genes to increase the intracellular levels of antibiotic biosynthetic enzymes. The invention also provides organisms comprising mutant biosynthetic genes which can be used to generate novel hybrid antibiotics and a method for generating these strains from cloned spiramycin biosynthetic genes.

The highly related macrolide antibiotics spiramycin and tylosin are produced by Streptomyces ambofaciens (NRRL 15263) and S. fradiae (ATCC 19609), respectively. Each is a 16-member cyclic lactone with three sugar residues. The antibiotic activity of spiramycin and tylosin, like that of other macrolides, is due to inhibition of protein synthesis by a mechanism that involves the binding of the antibiotic to the ribosome.

The present invention provides macrolide biosynthetic gene expression vectors for use in Streptomyces and other host cells. The development and exploitation of recombinant DNA technology in Streptomyces has been driven by the desire to improve the antibiotic-producing ability of this industrially important organism and to produce novel antibiotics. This development has been somewhat retarded by the low number of antibiotic biosynthetic genes presently available for use in modifying Streptomyces by recombinant DNA technology. The present invention is useful and especially important in that it expands the number of antibiotic biosynthetic genes suitable for such use.

The vectors of the present invention are particularly useful, because the vectors can be introduced into and selected for in a variety of Streptomyces cells. Streptomyces provides over half of the clinically important antibiotics and thus is a commercially significant group. The present invention provides new and useful vectors and methods not only for this industrially important group but also for other antibiotic-producing organisms, allows for increasing the yield of macrolide antibiotics in fermentations, and allows for producing new antibiotics and antibiotic derivatives.

For purposes of the present invention, as disclosed and claimed herein, the following terms are defined below.

AmR—the apramycin resistance-conferring gene.

Antibiotic—a substance produced by a microorganism which, either naturally or with limited modification, will inhibit the growth of or kill another microorganism or eukaryotic cell.

Antibiotic Biosynthetic Gene—a DNA segment that encodes one or more activities that are necessary in the biochemical process of converting primary metabolites into antibiotics.

Antibiotic Biosynthetic Pathway—the entire set of antibiotic biosynthetic genes necessary for the process of converting primary metabolites into antibiotics.

Antibiotic-Producing Organism—any organism, including, but not limited to, Actinoplanes, Actinomadura, Bacillus, Cephalosporium, Micromonospora, Penicillium, Nocardia, and Streptomyces, which either produces an antibiotic or contains genes which, if expressed, would produce an antibiotic.

Antibiotic Resistance-Conferring Gene—a DNA segment that encodes an enzymatic or other activity that confers resistance to an antibiotic.

ApR—the ampicillin resistance-conferring gene.

Bifunctional Cloning Shuttle Vector—a recombinant DNA cloning vector that can replicate and/or integrate into organisms of two different taxa.

BlR—the bleomycin resistance-conferring gene.

Cloning—the process of incorporating a segment of DNA into a recombinant DNA cloning vector and transforming a host cell with the recombinant DNA.

CmR—the chloramphenicol resistance-conferring gene.

Complementation—the restoration of a mutant strain to its normal phenotype by a cloned gene.

cos—the lambda cohesive end sequence.

Cosmid—a recombinant DNA cloning vector which is a plasmid that not only can replicate in a host cell in the same manner as a plasmid but also can be packaged into phage heads.

Gene—A DNA sequence that comprises a promoter, coding sequence, and terminator positioned so that the promoter drives transcription of the coding sequence and the terminator stops transcription.

Genetic Library—a set of recombinant DNA cloning vectors into which segments of DNA, representing substantially all DNA sequences of a particular organism, have been cloned.

Hybridization—the process of annealing two single-stranded DNA molecules to form a double-stranded DNA molecule, which may or may not be completely base-paired.

NmR—the neomycin resistance-conferring gene.

ori—a plasmid origin of replication.

Promoter—a DNA sequence that directs the initiation of transcription.

Recombinant DNA Cloning Vector—any autonomously replicating or integrating agent, including, but not limited to, plasmids, comprising a DNA molecule to which one or more additional DNA molecules can be or have been added.

Recombinant DNA Methodology—the alteration of a DNA sequence by point mutagenesis, insertion mutagenesis, deletion, or rearrangement.

Restriction Fragment—any linear DNA molecule generated by the action of one or more restriction enzymes.

Sensitive Host Cell—a host cell that cannot grow or whose growth is inhibited in the presence of a given antibiotic without a DNA segment that confers resistance thereto.

Srm gene—a DNA sequence which encodes a product involved in spiramycin antibiotic biosynthesis.

Subclone—a cloning vector with an insert DNA derived from another DNA of equal size or larger.

tac promoter—a hybrid of the trp and lac promoters.

TcR—the tetracycline-resistant phenotype or gene conferring same.

Terminator—the portion of a gene's DNA sequence that terminates transcription of DNA into RNA.

Transductant—a recipient host cell that has undergone transformation by recombinant phage infection.

Transformant—a recipient host cell that has undergone transformation.

Transformation—the introduction of DNA into a recipient host cell that changes the genotype and results in a change in the recipient cell.

tsrR—the thiostrepton-resistant phenotype or gene conferring same.

DETAILED DESCRIPTION OF THE INVENTION

Figure 1:
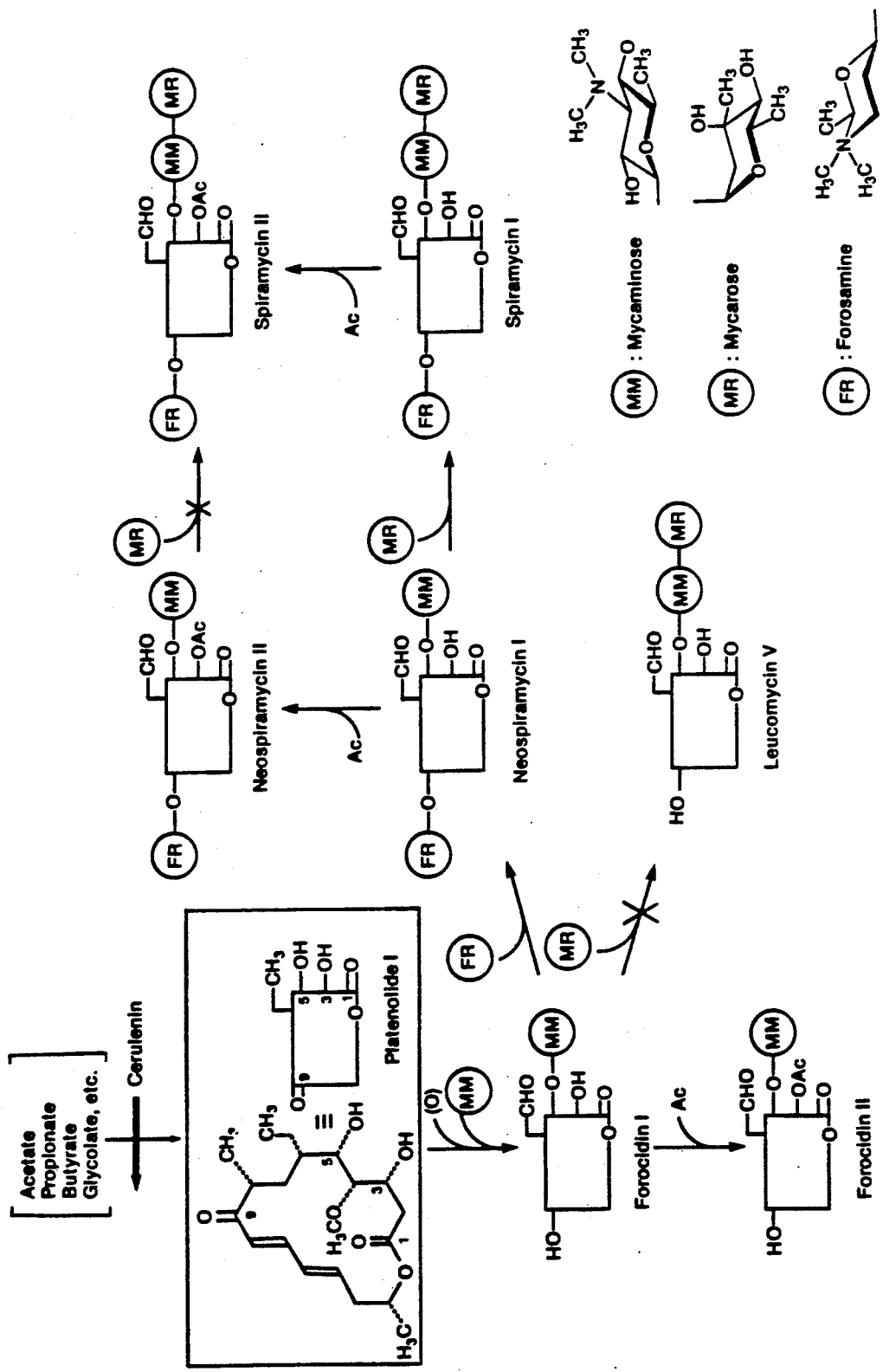
FIG. 1 is a depiction of the spiramycin antibiotic biosynthetic pathway of *Streptomyces ambofaciens*.

The present invention comprises novel macrolide antibiotic biosynthetic genes that can be used to increase antibiotic yield and to produce new antibiotics. The genes (srmD, srmE, srmF, srmG, and srmH) are useful in a method for increasing the levels of macrolide antibiotic, especially spiramycin (FIG. 1). The method comprises transforming the organism with a recombinant DNA vector that codes for expression of the gene product and culturing the transformed cell under conditions suitable for producing spiramycin.

Macrolide antibiotics are characterized by the presence of a highly branched macrocyclic lactone, the aglycone (See generally *Macrolide Antibiotics: Chemistry, Biology and Practice* (S. Omura, ed., Academic Press, New York)). Attached to the aglycone are one or more deoxy sugars. The sugars may be acylated. The macrocyclic ring is commonly 12-, 14-, or 16-membered but larger rings are also known. The mechanism of action of macrolide antibiotics involves the inhibition of protein synthesis.

The macrolide antibiotics are highly active against gram-positive organisms such as *Staphylococcus, Streptococcus*, and *Diplococcus* and also have activity against gram-negative organisms such as *Neisseria gonorroheae* and *meningitidis, Bordetella pertussis*, and *Haemophilus influenzae*. Id. at p.26. All of the above strains are capable of causing significant illnesses. Macrolides, including spiramycin and tylosin, have been used clinically in the medical and veterinary fields due to their low toxicity. Id. at p.27.

Because the macrolides are so clinically useful, it is of the utmost importance to clone the genes responsible for producing the enzymes of the respective biosynthetic pathways. These genes can be used to increase the enzyme concentration in an organism, thereby increasing the efficiency of antibiotic production. The genes may be shuttled among various antibiotic producers to generate hybrid antibiotics, due to the "loose" substrate specificities of some of the biosynthetic enzymes (Sadakane et al., 1982, J. Antibiotics 35:680–687). In addition, the cloned genes can serve as substrates for mutagenesis which can lead to alterations in substrate specificity. The genes can also be used to generate strains containing mutant genes by the method of the present invention.

*Streptomyces ambofaciens*, two illustrative strains of which are available from the Agricultural Research Service, Northern Regional Research Center (NRRL), Peoria, Ill., 61604, under the accession number NRRL 15263 and NRRL 2420, produces spiramycin, a 16-membered macrolide that contains three sugars: mycaminose, mycarose, and forosamine. The biosynthesis of spiramycin is detailed in FIG. 1.

Figure 2:
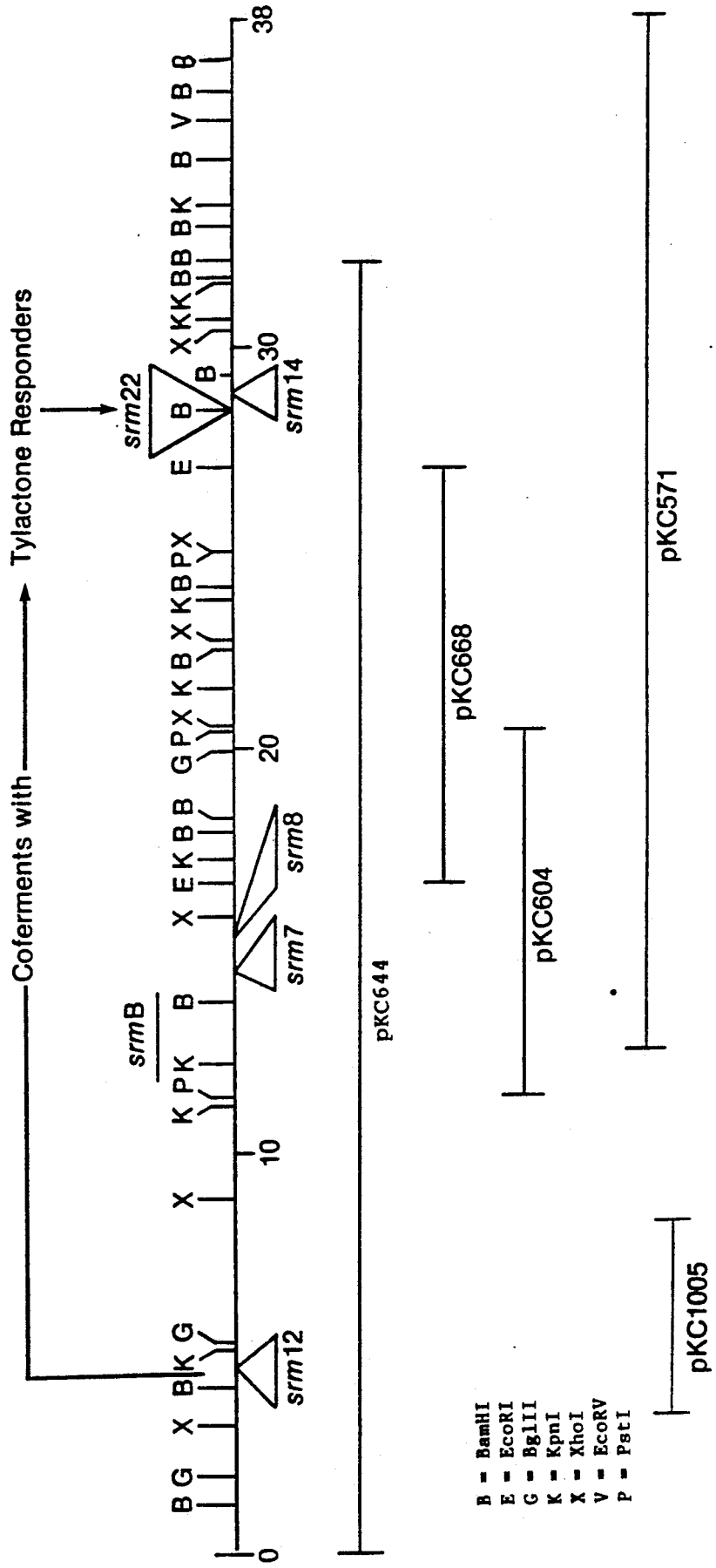
FIG. 2 is a restriction site map of the ~32 kb insert DNA of cosmid pKC644. Map positions of mutations carried by the srm mutant strains are shown together with the insert DNA of plasmids pKC604, pKC668, pKC1005, and cosmid pKC571.

The present invention comprises five spiramycin antibiotic biosynthetic genes located on a span of ~32 kb of the *Streptomyces ambofaciens* genome. The cosmid pKC644 has insert DNA which comprises this ~32 kb span. The insert fragment is the product of a partial MboI digest of *S. ambofaciens* DNA. This MboI fragment also comprises the srmB gene, a spiramycin antibiotic resistance-conferring gene disclosed in European Patent Publication No. 0154430. The location of the genes on the ~32 kb MboI fragment is shown in FIG. 2.

Figure 3:
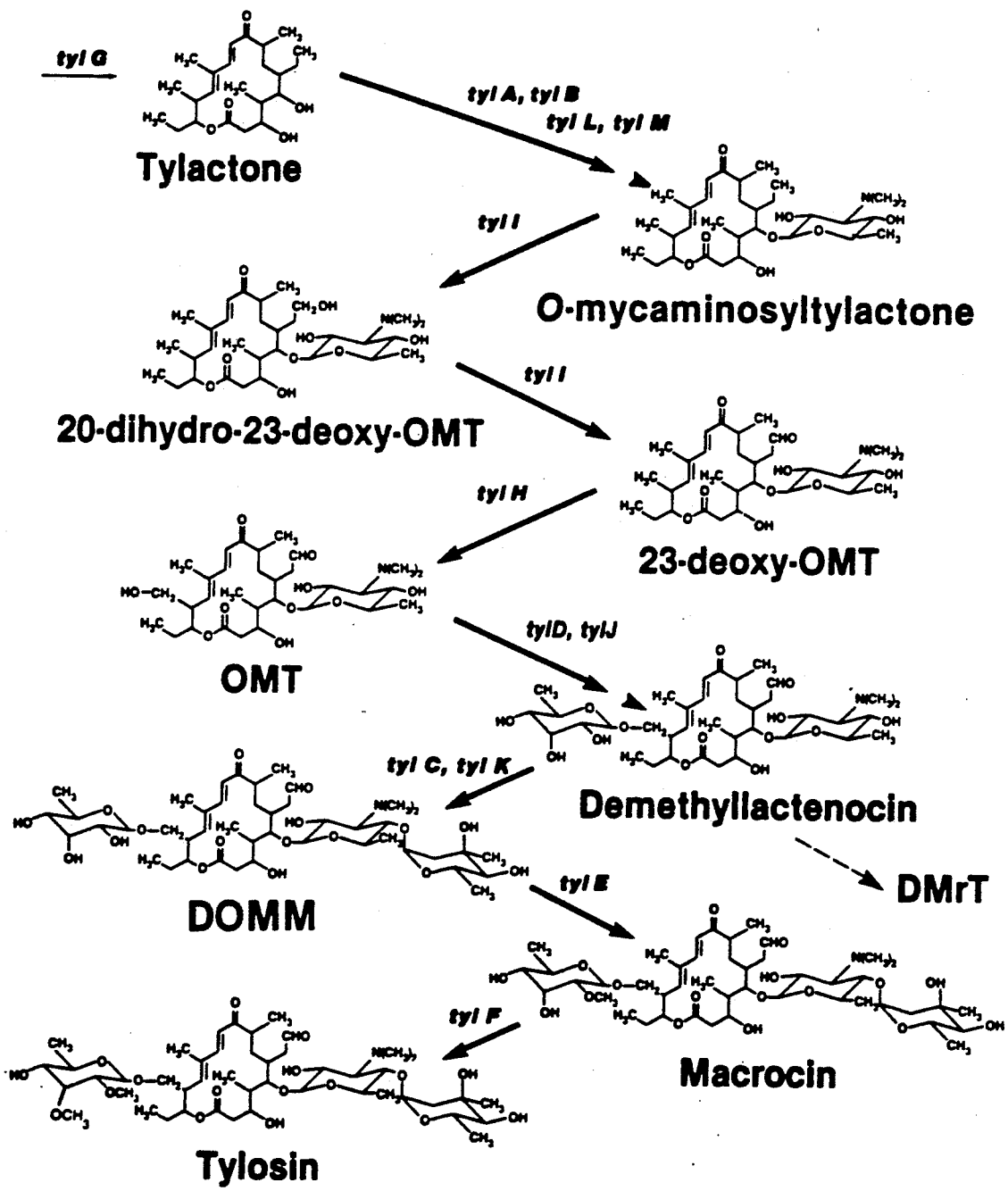
FIG. 3 is a depiction of tylosin antibiotic biosynthesis in *Streptomyces fradiae*.

The srmD gene encodes a gene product responsible for the biosynthesis or attachment of the three sugars to the aglycone. The srmD gene is comprised by the ~10 kb EcoRI fragment of the *S. ambofaciens* genome comprised by cosmid pKC644. An analogue to srmD is found in the tylA gene of *Streptomyces fradiae*. Strains carrying tylA mutations accumulate tylactone, the macrocyclic ring with no sugars attached (See FIG. 3 for a diagram of tylosin biosynthesis and Baltz and Seno, 1981, Antimicrob. Agents Chemother. 20:214–225). The srmD gene provides the biosynthetic activity lacking in tylA mutant strains.

The biosynthesis or attachment of mycaminose to the aglycone is carried out by the product of the srmE gene. The srmE gene is comprised by the ~10 kb EcoRI fragment of the *S. ambofaciens* genome comprised by cosmid pKC644. The srmE gene has a counterpart in the *S. fradiae* tylB gene. The srmE gene can supply by complementation the biosynthetic activity lacking in the tylB mutants. TylB mutant strains accumulate tylactone.

The srmF, srmG, and srmH genes are also involved in spiramycin antibiotic biosynthesis. The srmF gene is comprised by the ~5.5 kb XhoI fragment of the *S. ambofaciens* genome comprised by cosmid pKC644. This fragment is shown as the insert DNA of pKC1005 in FIG. 2. The srmF gene product provides an activity subsequent to lactone ring formation. The srmG gene is comprised by the ~9 kb PstI fragment of the *S. ambofaciens* genome comprised by cosmid pKC604. The srmH gene product is involved in aglycone formation. The srmH gene is comprised by the ~7 kb KpnI fragment of the *S. ambofaciens* genome comprised by cosmid pKC644.

The spiramycin biosynthetic genes of the present invention can be isolated from *E. coli* DK22 transformed with cosmid pKC644 (FIG. 2). This organism is available from the Agricultural Research Service, Northern Regional Research Center ("NRRL") Peoria, Ill., 61604 under accession number NRRL B-18238.

Figure 4:
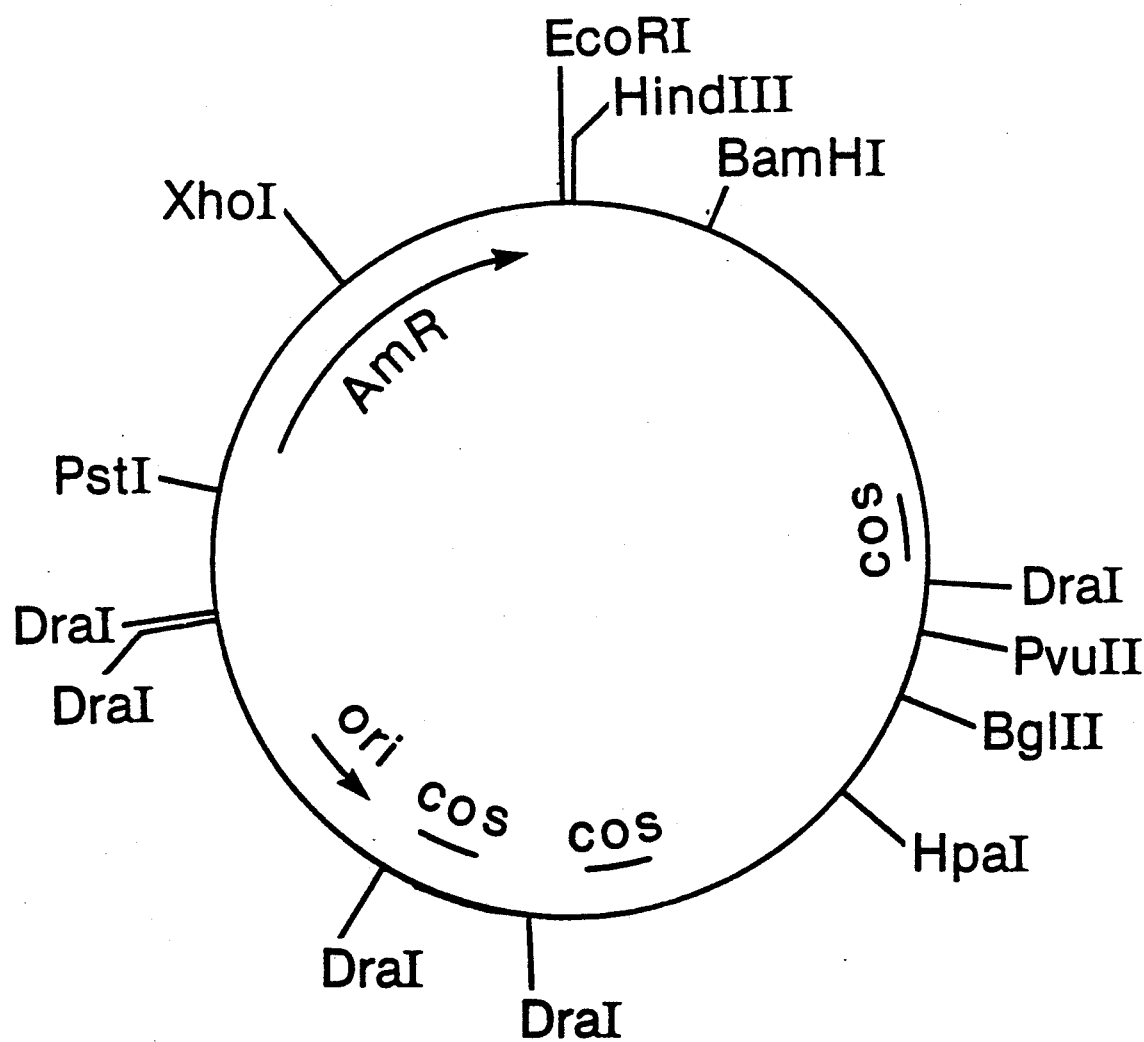
FIG. 4 is a restriction site and function map of plasmid pKC473, the vector backbone of pKC644.

Cosmid pKC644 was generated from a genomic cosmid library of *Streptomyces ambofaciens* DNA. Those skilled in the art will recognize appropriate methods for cloning genomic DNA partially digested by a restriction enzyme such as MboI. A typical method is described in Rao et al., 1987, in *Methods in Enzymology*, 153:166–198 (R. Wu and L. Grossman, eds. Academic Press, N.Y.). The insert DNA (~32 kb and FIG. 2) comprises the five macrolide antibiotic genes described above and the srmB spiramycin resistance genes. The vector backbone (pKC473) of cosmid pKC644 is shown in FIG. 4. The insert DNA was cloned into the HindIII site of cosmid pKC473.

Subclones of the insert DNA from pKC644 were constructed so as to comprise the specific genes. The present invention also provides subclones of each of the 5 srm biosynthetic genes. The subclones can be used to increase the intracellular concentration of the specific biosynthetic gene products by transformation of the subclone into a host cell. Each cloned gene can also be used to generate mutant strains deficient for the specific gene, another important aspect of the present invention.

Figure 5:
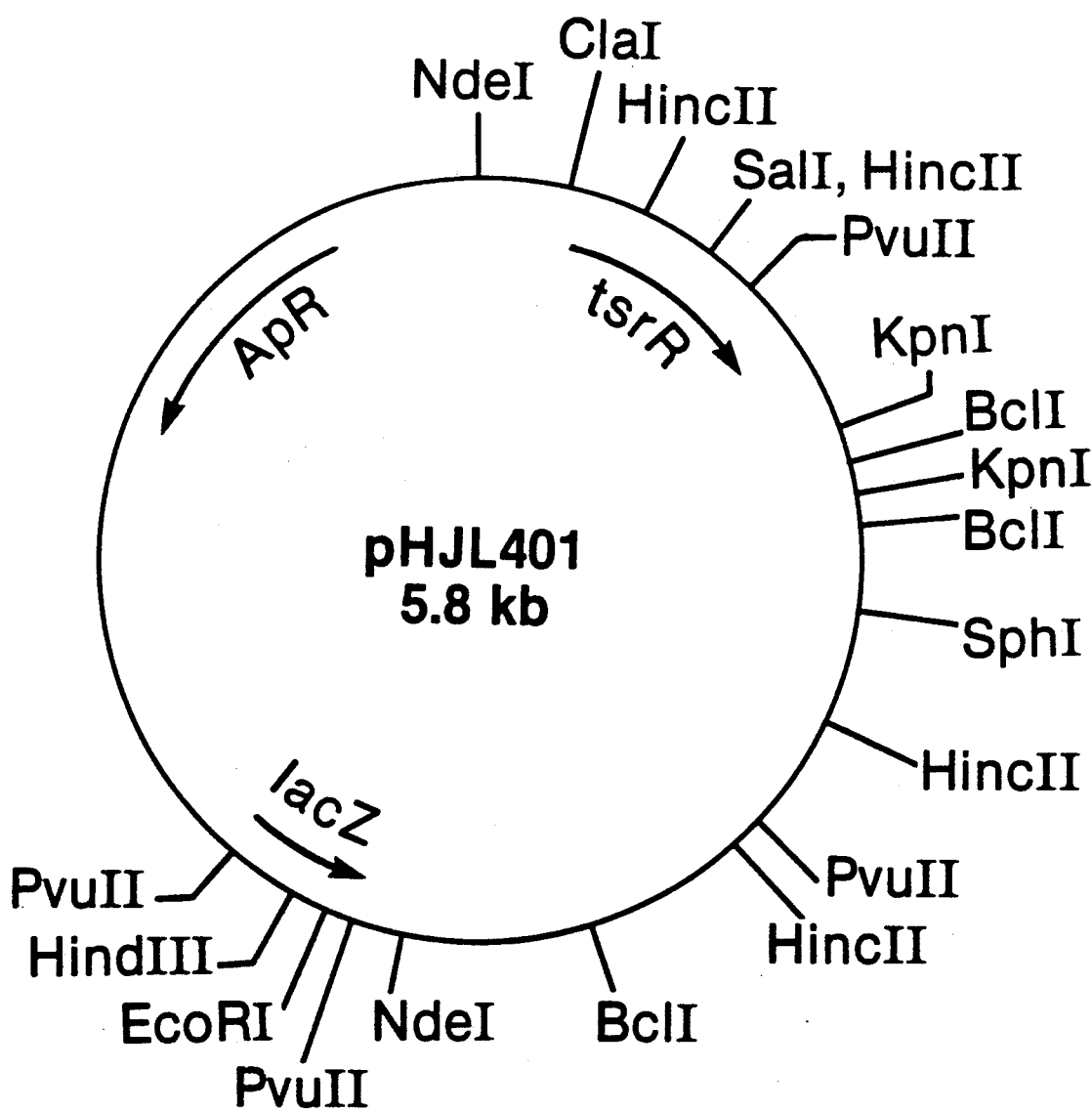
FIG. 5 is a restriction site and function map of plasmid pHJL401.
Figure 7:
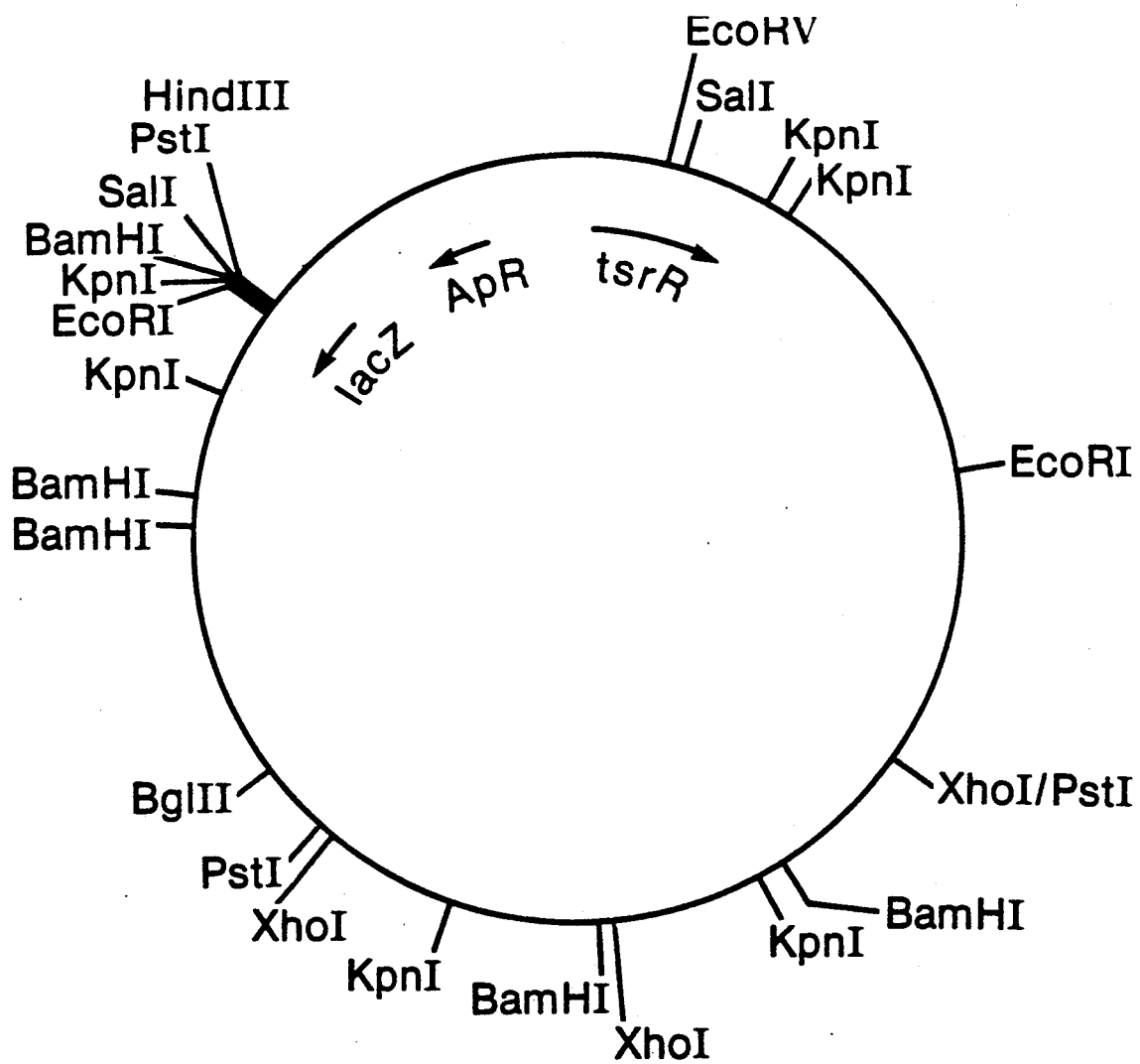
FIG. 7 is a restriction site and function map of plasmid pKC668.

The srmD and srmE genes can be isolated from plasmid pKC668 (FIG. 7). Plasmid pKC668 was generated by digesting cosmid pKC644 with restriction enzyme EcoRI, isolating the resulting ~10 kb EcoRI restriction fragment, and ligating the fragment with EcoRI-digested plasmid pHJL401 (FIG. 5). Plasmid pHJL401 is available from the NRRL under the accession number NRRL B-18217 and described in Larson and Hershberger, 1986, Plasmid 15:199-209. Because the ~10 kb EcoRI fragment was ligated to the vector pHJL401 in two orientations, the invention provides two illustrative plasmids that comprise the srmD gene, pKC668 and pKC668A. The orientation of the ~10 kb EcoRI fragment was determined by restriction enzyme analysis familiar to one skilled in the art.

Figure 9:
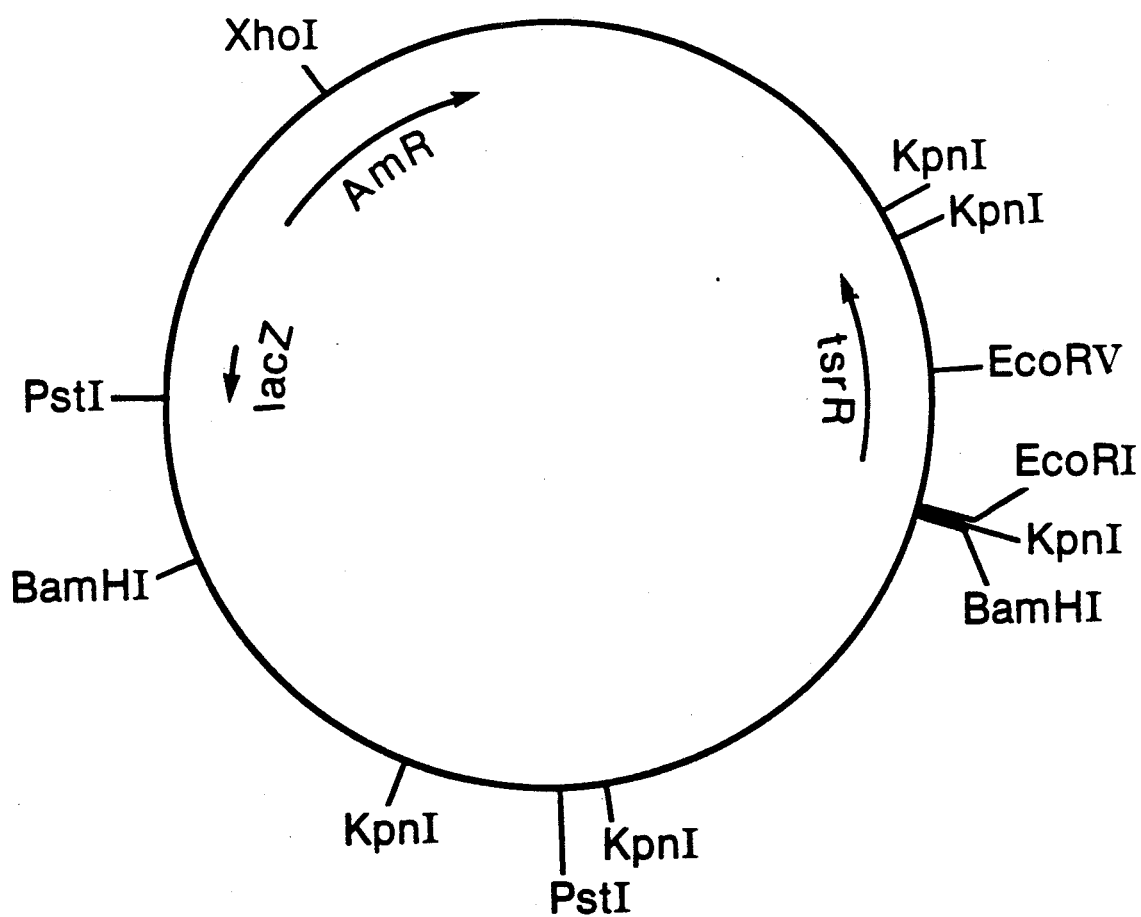
FIG. 9 is a restriction site and function map of plasmid pKC1005.

A srmF-containing plasmid can be constructed by digesting cosmid pKC644 with restriction enzyme XhoI, isolating the resulting ~5.5 kb XhoI fragment, and ligating it to plasmid pOJ160 partially digested with SalI (SalI ends are compatible with XhoI ends). Because the ~5.5 kb XhoI fragment can be ligated to SalI-digested pOJ160 in opposite orientations, the resulting ligation yields two plasmids, pKC1005 (FIG. 9) and pKC1005A. The orientation of the ~5.5 kb XhoI fragment can be determined by restriction enzyme analysis.

Figure 6:
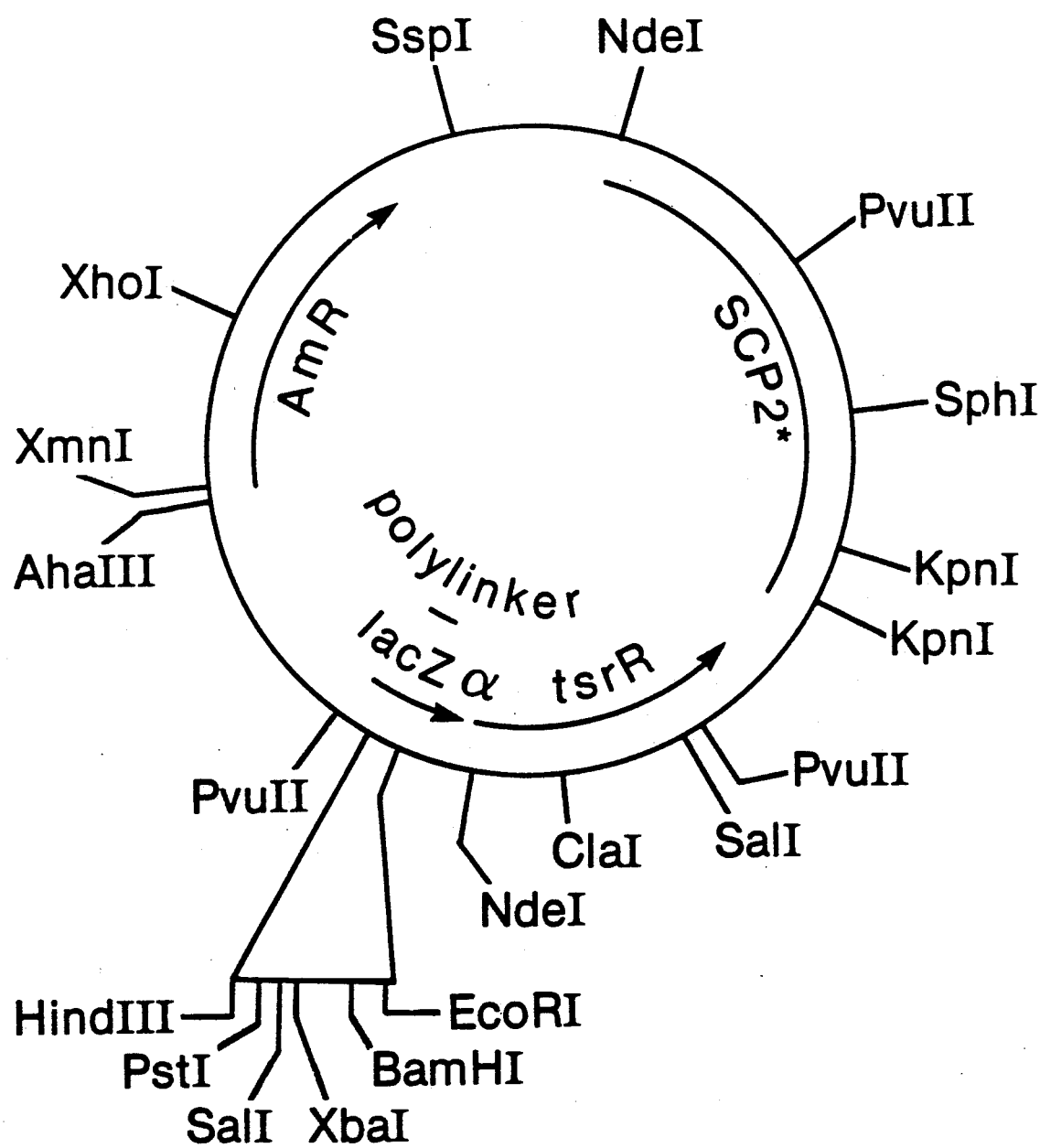
FIG. 6 is a restriction site and function map of plasmid pOJ160.
Figure 8:
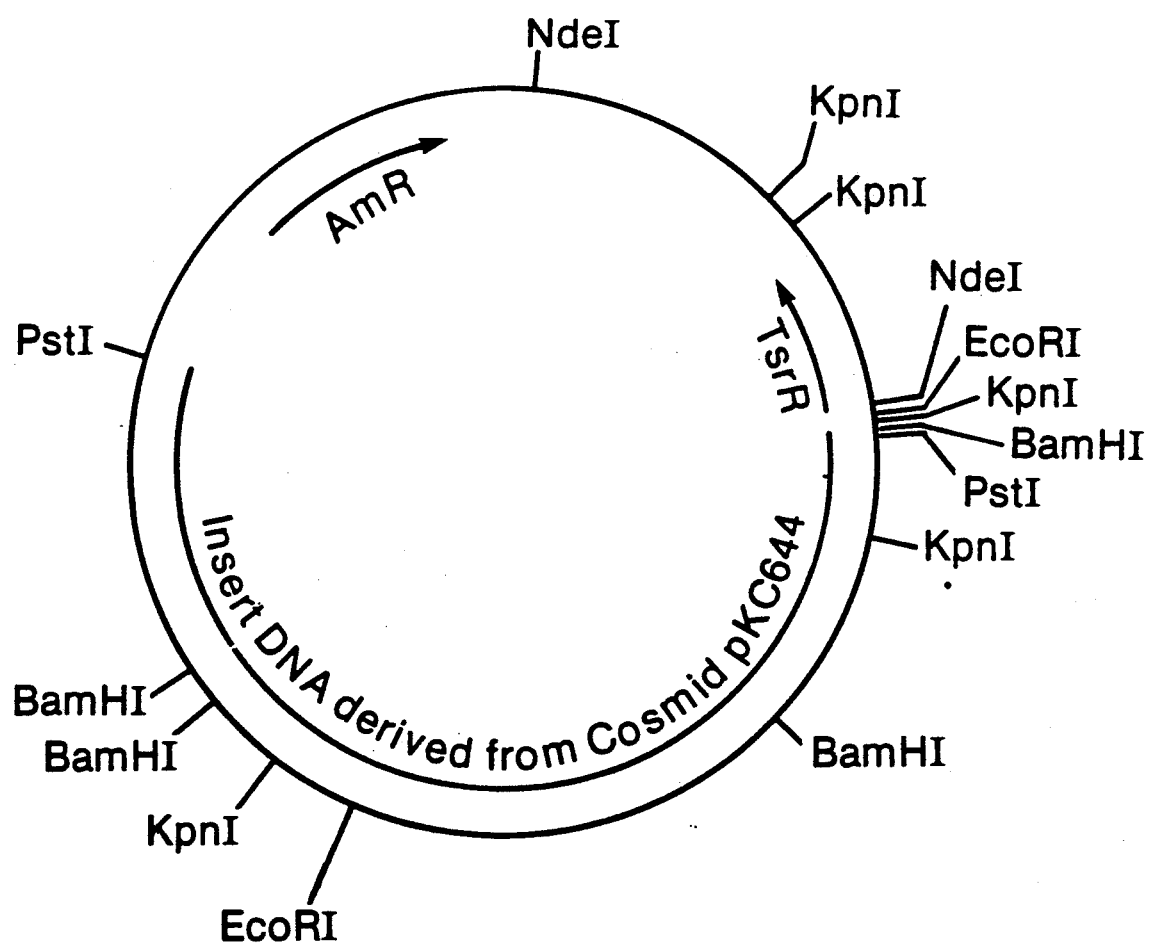
FIG. 8 is a restriction site and function map of plasmid pKC604.

Plasmid pKC604 (FIG. 8) is an illustrative vector of the invention that comprises the srmG gene. The plasmid was constructed by digesting cosmid pKC644 with restriction enzyme PstI, isolating the resulting ~9 kb PstI fragment, and ligating it to PstI-digested pOJ160, a plasmid available from the NRRL under the accession number NRRL B-18088 (FIG. 6). The ~9 kb PstI fragment was ligated to the vector in two orientations, yielding illustrative plasmids pKC604 and pKC604A. The orientation of the ~9 kb PstI fragment can be determined by restriction enzyme analysis.

The srmH gene can be isolated from cosmid pKC571 (see FIG. 2), available from the NRRL under accession number NRRL B-18237. Cosmid pKC571 also comprises the srmD, srmE, and srmG genes.

Those skilled in the art will recognize that a variety of techniques, i.e., partial digestion with restriction enzymes, can lead to the isolation of many combinations of the srmD, srmE, srmF, srmG and srmH genes. The many Streptomyces vectors available (see Table I) enables one skilled in the art to tailor insert, vector, and host cell combinations to fit various needs. One's choice of variables such as antibiotic resistance markers, origins of replication, and restriction enzyme sites can be met by the proper selection of a vector. The particular vectors exemplified are merely illustrative and do not limit the scope of the present invention.

TABLE I

| Streptomyces Plasmids | | |
|---|---|---|
| Plasmid | Host | Accession Number |
| SCP2 | *Streptomyces coelicolor* A3(2) | NRRL 15042 |
| SCP2* | *Streptomyces coelicolor* M110 | NRRL 15041 |
| pEL7 | *Streptomyces ambofaciens*/pEL7 | NRRL 12523 |
| pUC6 | *Streptomyces espinosus* | NRRL 11439 |
| pUC3 | Streptomyces 3022A | NRRL 11441 |
| SLP1 | *Streptomyces lividans* | NCIB[1] 11417 |
| pNM100 | *Streptomyces virginiae* | NRRL 15156 |
| pEL103 | *Streptomyces granuloruber* A399 12.13/pEL103 | NRRL 12549 |
| pIJ702 | *Streptomyces lividans* | ATCC[2] 39155 |

[1]National Collection of Industrial Bacteria (NCIB), Torry Research Station, Post Office Box 31, 135 Abbey Road, Aberdeen AB98DG, Scotland, United Kingdom.
[2]American Type Culture Collection, Rockville, MD 20852.

Therefore, the present invention is not limited to a particular vector comprising the antibiotic genes of the invention but rather encompasses the biosynthetic genes in whatever vector is used to introduce the genes into a recombinant host cell.

Those skilled in the art will recognize that the srmD, srmE, srmF, srmG, and srmH sequences from pKC644 as available under accession number NRRL B-18238 can be used to prepare DNA probes for use in obtaining other biosynthetic gene-containing segments, especially segments encoding macrolide biosynthetic genes. In addition, due to the diversity of *Streptomyces ambofaciens* strains both in nature and the laboratory, there will be a variety of allelic variants of the srm genes that can be readily isolated given the srm gene-containing compounds of this invention. These allelic variants, which encode gene products with amino acid residue sequences that differ from that of the srm gene products, are functionally equivalent to the srm genes of the present invention and are meant to be encompassed by the term srm genes as used herein.

Similarly, due to the degeneracy of the genetic code, those skilled in the art are familiar with synthetic methods of preparing DNA sequences which may code for the same or functionally the same activity as that of the natural gene sequence. Likewise, those skilled in the art are familiar with techniques for modifying or mutating the gene sequence to prepare new sequences which encode the same or substantially the same polypeptide activity as the natural sequences. Consequently, these synthetic mutant and modified forms of the genes and expression products of these genes are also meant to be encompassed by the present invention.

A representative list of strains from which macrolide antibiotic genes can be isolated is given in Table II along with the antibiotics produced by the strains. In addition, the representative strains of Table II are good host organisms in which to introduce srm genes to produce novel antibiotics.

TABLE II

| Macrolide, Lincosamide, and Streptogramin Antibiotic-Producing Organisms | |
|---|---|
| Organism | Antibiotic |
| *Micromonospora* | rosaramicin |

TABLE II-continued

Macrolide, Lincosamide, and Streptogramin Antibiotic-Producing Organisms

| Organism | Antibiotic |
| --- | --- |
| rosaria | |
| Streptomyces | |
| albireticuli | carbomycin |
| albogriseolus | mikonomycin |
| albus | albomycetin |
| albus var. coilmyceticus | coleimycin |
| ambofaciens | spiramycin and foromacidin D |
| antibioticus | oleandomycin |
| avermitilis | avermectins |
| bikiniensis | chalcomycin |
| bruneogriseus | albocycline |
| caelestis | M188 and celesticetin |
| cinerochromogenes | cineromycin B |
| cirratus | cirramycin |
| deltae | deltamycins |
| djakartensis | niddamycin |
| erythreus | erythromycins |
| eurocidicus | methymycin |
| eurythermus | angolamycin |
| fasciculus | amaromycin |
| felleus | argomycin and picromycin |
| fimbriatus | amaromycin |
| flavochromogenes | amaromycin and shincomycins |
| fradiae | tylosin |
| fungicidicus | NA-181 |
| fungicidicus var. espinomyceticus | espinomycins |
| furdicidicus | mydecamycin |
| goshikiensis | bandamycin |
| griseofaciens | PA133A and B |
| griseoflavus | acumycin |
| griseofuscus | bundlin |
| griseolus | griseomycin |
| griseospiralis | relomycin |
| griseus | borrelidin |
| griseus ssp. sulphurus | bafilomycins |
| halstedi | carbomycin and leucanicidin |
| hygroscopicus | tylosin |
| hygroscopicus subsp. aureolacrimosus | milbemycins |
| kitastoensis | leucomycin A3 and josamycin |
| lavendulae | aldgamycin |
| lincolnensis | lincomycin |
| loidensis | vernamycin A and B |
| macrosporeus | carbomycin |
| maizeus | ingramycin |
| mycarofaciens | acetyl-leukomycin, and espinomycin |
| narbonensis | josamycin and narbomycin |
| narbonensis var. josamyceticus | leucomycin A3 and josamycin |
| olivochromogenes | oleandomycin |
| platensis | platenomycin |
| rimosus | tylosin and neutramycin |
| rochei | lankacidin and borrelidin |
| rochei var. volubilis | T2636 |
| roseochromogenes | albocycline |
| roseocitreus | albocycline |
| spinichromogenes var. suragaoensis | kujimycins |
| tendae | carbomycin |
| thermotolerans | carbomycin |
| venezuelae | methymycins |
| violaceoniger | lankacidins and lankamycin |

The present invention provides a method for increasing the antibiotic biosynthetic ability of an organism, whereby a recombinant plasmid comprising one or more spiramycin biosynthetic genes is transformed into a host cell under conditions which allow the expression of the biosynthetic genes. If desired, large yields of biosynthetic enzyme can be achieved with a high copy number plasmid. The vectors of the present invention can be used to transform a variety of organisms to increase the spiramycin-producing ability of the organism. In addition, the genes can be used to transform a variety of antibiotic-producing organisms, particularly macrolide antibiotic-producing organisms, for purposes of making novel antibiotics. The previous Table presents a representative sampling of various antibiotic-producing organisms in which the srmD, srmE, srmF, srmG, and srmH genes can be used either to produce a novel antibiotic or to increase antibiotic production.

The spiramycin biosynthetic genes function particularly well in Streptomyces ambofaciens and S. fradiae. Yet even if the original genes failed to express in a given organism, such as E. coli, because, for example, the Streptomyces promoter failed to function in that organism, the srmD, srmE, srmF, srmG, and srmH coding sequences of the present invention could be ligated to a DNA sequence containing an appropriate promoter and ribosome-binding site to achieve expression of the srmD, srmE, srmF, srmG, and srmH genes in the host of choice.

The srm genes can be used in biosynthetic pathways other than spiramycin. One illustrative use is to increase tylosin production in Streptomyces fradiae. Tylosin is an antibiotic made by Streptomyces fradiae. It differs from spiramycin in several respects, including the lack of forosamine at C-9 of the lactone ring, the presence of mycinose at the C-23 hydroxyl group, and the lack of acylation at the C-4 hydroxyl group. Mutant S. fradiae tylA strain GS14 (NRRL 12188) is blocked in the formation of all three sugars. The tylB mutant strains GS50 (NRRL 12201) and PM73 are blocked in the synthesis or attachment of mycaminose. The tylA and tylB mutations have been shown to reside in separate genes by differing responses to co-fermentation with other tylosin biosynthetic pathway mutant strains (Baltz and Seno, supra). The srmD and srmE genes provide tylA and tylB activity, respectively.

Illustrative plasmid pKC668 of this invention comprises the srmD and srmE genes. Plasmid pKC668 was transformed into both NRRL 12188 (tylA mutant) and NRRL 12201 (tylB mutant). Because both transformants produced tylosin, the srmD and srmE gene products can substitute for the tylA and tylB genes, respectively. Strains where similar results can be achieved are found in Table II.

Illustrative vectors of the present invention can be constructed even when not flanked by restriction sites that match restriction sites in the cloning vector. Restriction fragments used to construct vectors illustrative of the present invention can be conventionally modified, by means familiar to one skilled in the art, to facilitate ligation. For example, molecular linkers can be provided to a particular spiramycin gene-containing restriction fragment or to DNA comprising vector replication or integration functions. Thus, specific sites for subsequent ligation can be conveniently constructed. In addition, the various spiramycin biosynthetic gene-containing restriction fragments, origin of replication, or sequences that provide for chromosomal integration of a given vector can be modified by adding, eliminating, or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose. It is also noteworthy that a given spiramycin biosynthetic gene-containing restriction fragment is not limited to a particular position on a cloning vector, as long as critical, vector-controlled functions are not disrupted. Those skilled in the art understand or can readily determine which sites on a vector are advantageous for the ligation or insertion of a particular spiramycin gene-containing restriction fragment.

Of course, the spiramycin biosynthetic gene can be used to construct vectors other than plasmids. Phage φC31 is a well-known Streptomyces phage that is an excellent source of starting material for constructing integrative vectors that further exemplify the present invention. A derivative of phage φC31, phasmid pKC331, is especially preferred for constructing such integrating vectors and can be obtained from *E. coli* K12 BE447/pKC331 (NRRL B-15828). φC31-type phages are integrative vectors and can be readily modified to incorporate the spiramycin biosynthetic genes and thus confer spiramycin biosynthetic activity to Streptomyces. The present invention thus is not limited by the type of vector used to introduce the spiramycin biosynthetic genes into the target host cell nor by the location of the spiramycin biosynthetic genes once introduction has occurred.

The vectors of the present invention comprise DNA encoding one or more of the spiramycin antibiotic biosynthetic genes. Because amplification and manipulation of plasmids is done faster and more efficiently in *E. coli* than in Streptomyces, it is convenient to add DNA sequences that also allow for replication in *E. coli*. Thus, the addition of functional replicon-containing and antibiotic resistance-conferring restriction fragments from *E. coli* plasmids such as, for example, pUC8, pUC18, pUC19, pBR322, pACYC184, pBR325, pBR328, and the like is highly advantageous and adds to the general utility of the present illustrative vectors.

The cloning vectors and transformants of the present invention provide for the cloning of genes to improve yields of various products that are currently produced in Streptomyces and related cells. The present invention also provides selectable vectors that are useful for cloning, characterizing, and reconstructing a variety of useful DNA sequences.

The genes and vectors of the present invention provide the means to generate novel antibiotics. Particularly good hosts are mutant strains which accumulate intermediates in an antibiotic biosynthetic pathway. Such strains may be transformed with one or more genes of the present invention. The gene products may then carry out bioconversion of the intermediate to a novel hybrid antibiotic.

Spiramycin antibiotic mutant strains are useful to generate novel antibiotics. The hybrid antibiotics can be made by supplementing the mutant strains with novel substrates or transforming the strains with macrolide antibiotic biosynthetic genes. The present invention provides such mutant strains. The srm mutant strains can be generated by mutating one or more of the cloned srm genes by any number of standard recombinant DNA techniques, including but not limited to deletion, point mutation caused by chemicals such as nitrosoguanidine, nitrous acid, or hydroxylamine, and insertion mutagenesis. Insertion mutagenesis is a preferred method because one can select for the insertion of a marker gene. The mutated gene can be transformed into a host cell and then inserted into the chromosome by homologous recombination, yielding mutant strains. Illustrative examples are mutant strains of srmF, srmG and srmH.

An illustrative srmF mutant strain provided by this invention is designated srm-12. Srm-7 and srm-8 are two separate mutant strains carrying a non-functional srmG gene. The class of srmH mutant strains also includes two distinct insertions in the srmH gene, srm-14 and srm-22. FIG. 2 provides a diagram of each insertion. Each gene is defective due to insertion mutations. Unlike point mutations, insertion mutations do not revert to the wild-type state. The mutant strains provided by this invention are extremely stable. The mutant strains are generated by the transformation of the specific vector into the Tn10 hopping strain followed by transposon mutagenesis of the cloned DNA. The cloned DNA is then transformed into a macrolide antibiotic-producing host cell, and the mutant DNA is inserted into the host cell genome by homologous recombination.

Mutant strains may be used in several ways to generate novel hybrid antibiotics. First, they may accumulate intermediates which themselves have anti-microbial activity. Second, as shown above, the intermediates may serve as potential substrates for bioconversion when a suitable host cell is transformed with foreign genes. Third, supplementation of the mutants with unusual substrates can be used to generate novel antibiotics. The present invention provides such an example. When the illustrative srm-14 and srm-22 mutant strains (srmH mutant) are supplied with tylactone, a precursor in the tylosin pathway, an antibiotic other than spiramycin is synthesized.

The srmF mutant strain (srm-12) co-ferments with the srmH mutant strains (srm-14 and srm-22) to produce spiramycin. The srmH mutant strains respond to tylactone supplementation but the srmF mutant strains do not. The srmG mutant strains (srm-7 and srm-8) do not co-ferment with these mutants nor do they respond to supplementation. The mutants can be generated as described in Examples 10-13.

The present invention also provides a method for making mutant strains with altered macrolide biosynthetic genes. The method utilizes in vivo transposon mutagenesis of cloned spiramycin biosynthetic gene DNA, followed by introduction of the mutated DNA into a macrolide-producing Streptomyces chromosome. Cloned spiramycin insert DNA is introduced in the *E. coli* Tn10 hopping strain BE1997, available from the NRRL under accession number NRRL B-18372.

The hopping strain includes: (i) an F' element comprising a Tn10 element which includes NmR and BlR as selectable markers; (ii) a TcR plasmid pACYC184, comprising a transposase gene under the control of the IPTG-inducible tac promoter; and (iii) a defective lambda phage cI857 which will package pKC644 or any cosmid upon heat induction. The resulting strain is first treated with 1 mM IPTG to initiate random transposition of the resistance genes. Heat induction at 45° C. derepresses the cI857 repressor and generates phage particles carrying recombinant vector DNA with insertions in the cloned insert DNA. A phage lysate is made and introduced into any standard λ-sensitive *E. coli* strain. Selection is made on apramycin and bleomycin. Plasmid DNA from these transductants is analyzed by restriction enzyme digestions to identify insertions into the cloned DNA.

The mutated DNA is then transformed into a macrolide antibiotic producing Streptomycete. Homologous recombination by double cross-over yields organisms which can be identified and isolated. The recombinant vector carries an antibiotic resistance marker gene on its backbone and the neomycin resistance gene inserted into the cloned DNA. A double cross-over will leave the neomycin resistance gene in the chromosome and will excise the vector backbone. Therefore, selection for neomycin resistance will yield organisms where the chromosome has undergone at least one recombination event. The desired second cross-over is demonstrated by screening for sensitivity to the antibiotic resistance marker on the vector backbone. This ensures that none of the vector backbone will be present in the host chromosome. The resulting cells will be mutant for the gene carried on the original cosmid. Those skilled in the art will recognize that the present invention is not limited by the named antibiotic resistance genes exemplified herein.

The method is particularly well suited to isolate strains mutant for spiramycin biosynthetic genes. Mutants in antibiotic biosynthetic genes are selected by the lack of antibiotic production by conventional methods. The mutant strains of the present invention, deficient in spiramycin antibiotic biosynthesis were isolated via this method as detailed in Examples 9-12. The method also allows the easy cloning of the mutated sequence and thus provides a means of cloning the wild type gene.

The invention provides a method of generating a host cell that comprises an altered antibiotic biosynthetic gene where said method comprises:

(1) changing the nucleotide sequence of a spiramycin biosynthetic gene by recombinant DNA methodology;

(2) transforming said gene of step (1) into an antibiotic-producing host cell; and (3) identifying the transformed cells of step (2) that have incorporated the altered gene of step (1) through a process of homologous recombination.

Streptomyces can be cultured in a number of ways using any of several different media. Preferred carbohydrate sources in a culture medium include, for example, molasses, glucose, dextrin, and glycerol. Nitrogen sources include, for example, soy flour, amino acid mixtures, and peptones. Nutrient inorganic salts are also incorporated and include the customary salts capable of yielding sodium, potassium, ammonium, calcium, phosphate, chloride, sulfate, and like ions. As is necessary for the growth and development of other microorganisms, essential trace elements are also added.

The following examples further illustrate and describe the invention disclosed herein. The invention is not limited in scope by reason of any of the following Examples; sources of reagents or equipment are provided merely for convenience and in no way limit the invention. Both an explanation of and the actual procedures for constructing the invention are described where appropriate.

EXAMPLE 1

Isolation of Cosmid pKC644

Figure 10:
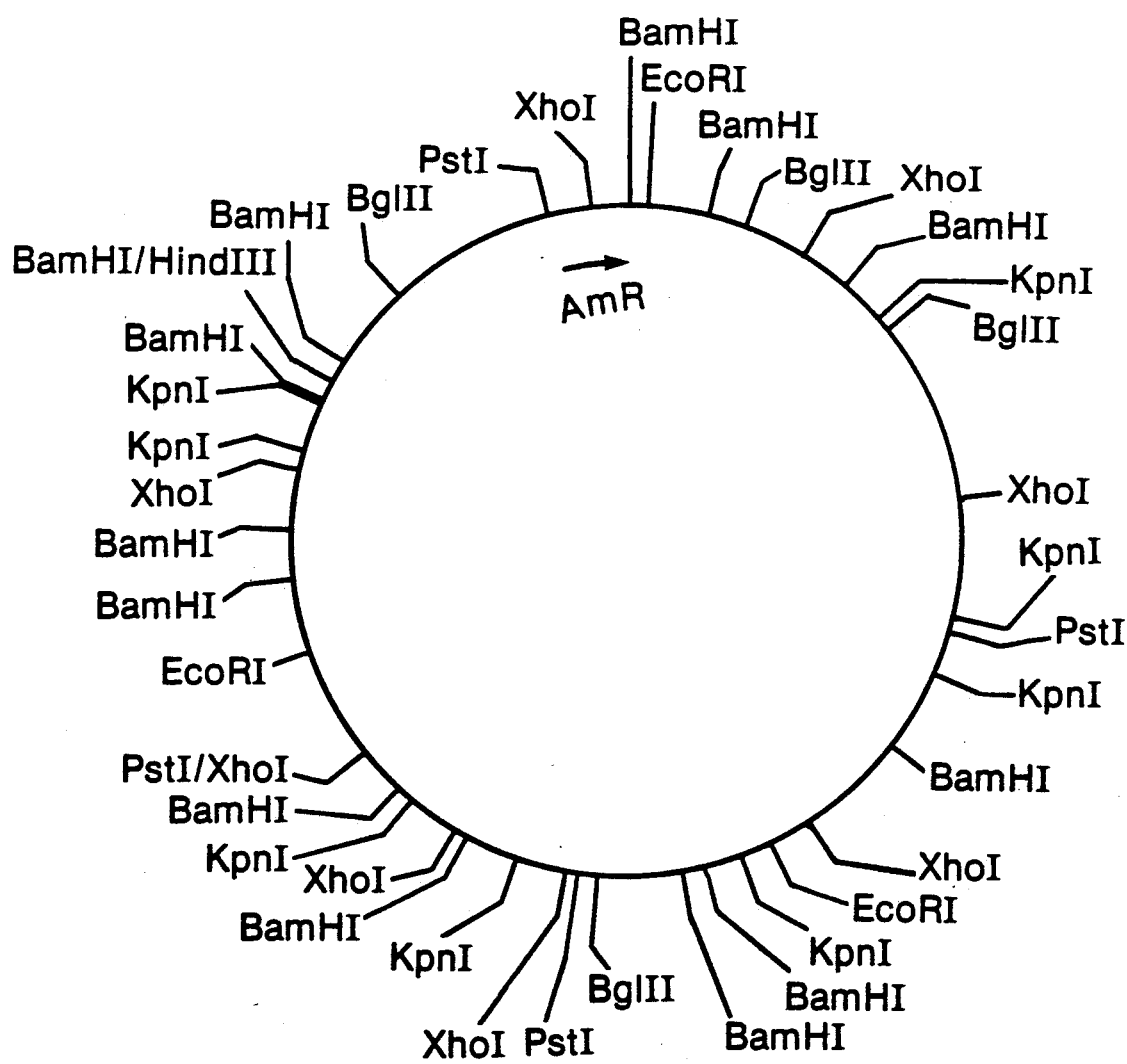
FIG. 10 is a restriction site and function map of cosmid pKC644.
Figure 11:
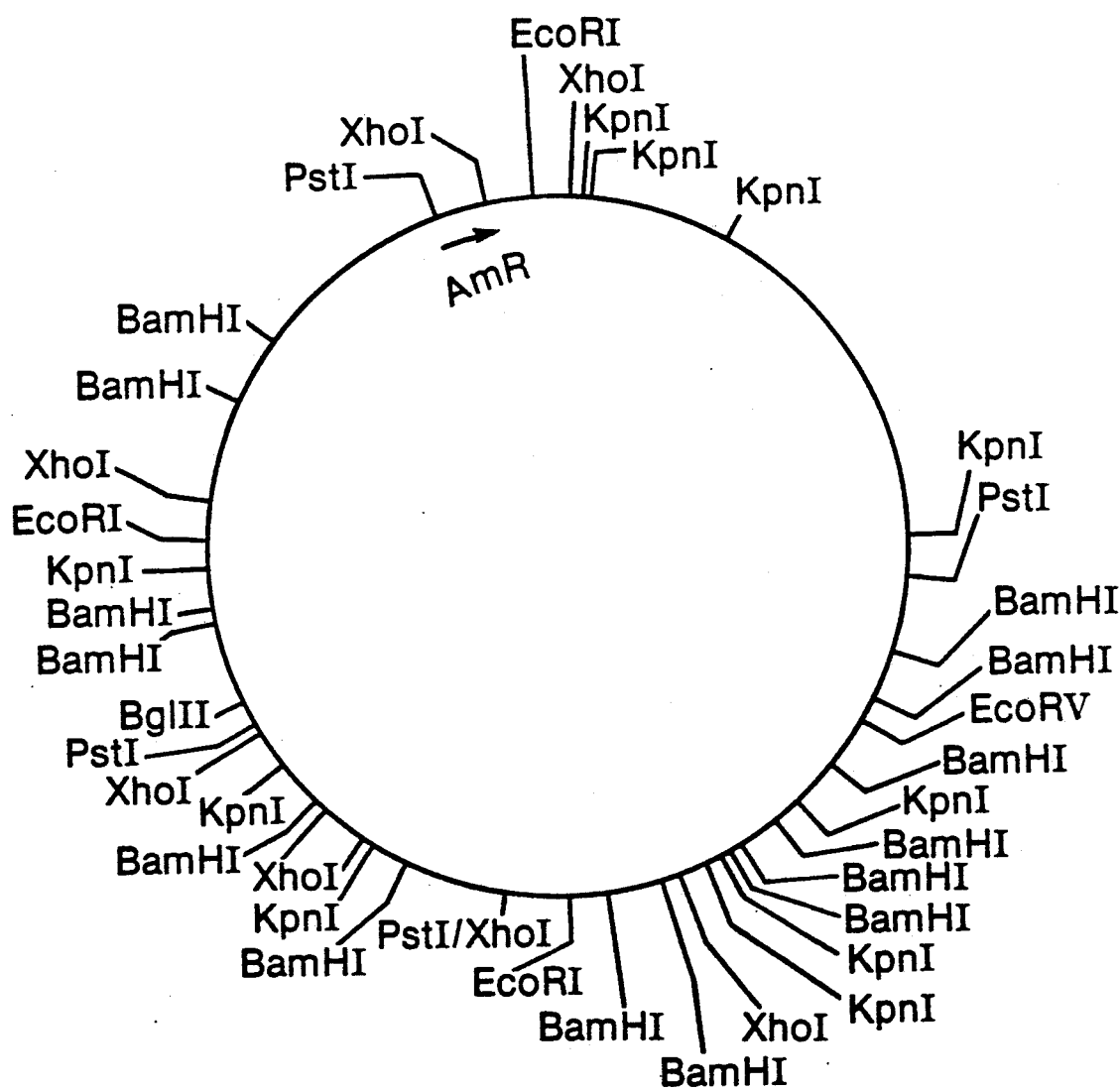
FIG. 11 is a restriction site and function map of cosmid pKC571.

Cosmid pKC644 (FIG. 10) can be obtained from the Northern Regional Research Center (NRRL), Peoria, Ill. 61604, in E. coli K12 DK22 under the accession number NRRL B-18238. The pKC644 cosmid DNA was used to isolate genes of the present invention and to generate spiramycin biosynthetic mutant strains. The lyophils of E. coli K12 DK22/pKC644 were plated onto L-agar plates (10 g of tryptone, 10 g of NaCl, 5 g of yeast extract, and 15 g of agar per liter) containing 200 $\mu$g/ml apramycin to obtain a single colony isolate of the strain. This colony was used to inoculate about 500 ml of L broth (L agar without agar) containing 200 $\mu$g/ml apramycin, and the resulting culture was incubated at 30° C. with aeration until the cells reached stationary phase.

Cosmid DNA was obtained from the cells in accordance with the procedure of Rao et al., 1987 in Methods in Enzymology, 153:166-198 (R. Wu and L. Grossman, eds., Academic Press, N.Y.), described below.

The cells were centrifuged at 8000 rpm for 10 minutes. After the supernatant was decanted, the cells were resuspended in 7 ml of 25% sucrose, 50 mM Tris.HCl, pH 8.0. Freshly prepared lysozyme (0.25 ml of a 5 mg/ml solution) was added to the solution, along with 0.4 ml of 0.5M EDTA (pH 8), and 0.05 ml of 5 mg/ml RNase A. The mixture was incubated for 15 minutes at 37° C. To this 0.75 ml of Triton lytic mix (150 mM Tris.HCl, pH 8.0, 3% Triton X-100 ®, 200 mM EDTA) was added, mixed, and incubated for 15 minutes on ice. If lysis was not complete, it was further incubated for about 5 minutes at 37° C. The mixture was centrifuged at 20,000 rpm for 40 minutes. The supernatant was removed and retained. A CsCl gradient (density of 1.55) was made by adding 28.65 of CsCl to 31.2 ml of DNA solution. The gradient solution was mixed to dissolve and transferred to large ultracentrifuge tubes. The tubes were filled with ~0.6 ml of ethidium bromide (10 mg/ml), sealed and mixed.

The gradient was centrifuged at 49,000 rpm for 18 hours. The lower band of plasmid DNA as visualized with long-wave UV light was collected. The ethidium bromide was removed by extracting 4 to 5 times with isoamyl alcohol. The DNA solution was dialyzed against 2 liters of TE buffer (10 mM Tris.HCl, pH 8.0, 1 mM EDTA) and after 2 hours was replaced with fresh TE. The dialyzed solution was extracted twice with phenol and twice with chloroform:isoamyl alcohol (24:1). The DNA was ethanol precipitated by adding one-tenth volume of 3M sodium acetate and 3 volumes of ethanol. The DNA was collected by centrifugation for 10 minutes at 10,000 rpm, washed with 70% ethanol and then 100% ethanol, dried and dissolved in about 250 $\mu$l of sterile TE. The concentration and purity was estimated by measuring optical density at 260 and 280 nm. A restriction site and function map of the insert DNA of pKC644 is presented in FIG. 2 of the accompanying drawings.

EXAMPLE 2

Construction of Plasmid pKC668

A. Isolation of Plasmid pHJL401

Plasmid pHJL401 (Larson and Hershberger, 1986, Plasmid 15:199-209) can be obtained from the NRRL in E. coli K12 JM109 under the accession number NRRL B-18217. Plasmid pHJL401 is a useful vector because it can replicate in E. coli or Streptomyces and it comprises two antibiotic resistance markers, ampicillin and thiostrepton. Thiostrepton is selectable only in Streptomyces; ampicillin is selectable in E. coli. Plasmid pHJL401 also has a polylinker multiple cloning site region in the lacZ gene. DNA inserts can thus be selected by picking white colonies when the cells are plated on Xgal (See Example 2B). The lyophils of *E. coli* K12 JM109/pHJL401 were plated onto L-agar plates containing 100 μg/ml ampicillin, 40 μg Xgal/ml, and 40 μg IPTG/ml to obtain a single blue colony isolate of the strain. This colony was used to inoculate about 500 ml of L broth containing 100 μg/ml ampicillin, and the resulting culture was incubated at 37° C. with aeration until the cells reach stationary phase.

Plasmid DNA was obtained from the cells to use in construction of plasmid pKC668 in substantial accordance with the procedure set forth in Example 1, above. A restriction site and function map of plasmid pHJL401 is presented in FIG. 5 of the accompanying drawings.

B. Final Construction of Plasmid pKC668

Plasmid pKC668 is an illustrative vector that comprises the srmD and srmE genes. The plasmid was constructed in the following manner. About 10 μg (10 μl) of plasmid pHJL401 DNA were added to 2 μl of 10X EcoRI buffer (1M Tris-HCl, pH=7.5; 0.5M NaCl; and 50 mM MgCl$_2$), 6 μl of H$_2$O, and 2 μl (~40 units; unit definitions herein correspond to those of New England Biolabs (NEB), 32 Tozer Road, Beverly, Mass. 01915-9990, unless otherwise indicated) of restriction enzyme EcoRI. The resulting reaction was incubated at 37° C. for two hours. The EcoRI-digested plasmid pHJL401 DNA was extracted and then collected by adjusting the sodium acetate (NaOAc) concentration of the reaction mixture to 0.30M, adding 2.5 volumes of ethanol, chilling the reaction mixture to −70° C., and centrifuging to pellet the precipitated DNA. The pellet of EcoRI-digested plasmid pHJL401 DNA was resuspended in 400 μl of TE buffer. About 1 μl (0.1 unit) of bacterial alkaline phosphatase (International Biotechnology, Inc. (IBI), P.O. Box 1565, New Haven, Conn. 06506) was added to the DNA solution, and the reaction was incubated at 65° C. for 1 hour. The reaction mixture was extracted with 400 μl of a 1:1 solution of phenol:chloroform and then extracted with 400 μl of chloroform. The EcoRI-digested, dephosphorylated plasmid pHJL401 DNA was collected by ethanol precipitation and centrifugation as described above, and the DNA pellet was resuspended in 10 μl of TE buffer.

About 10 μg of cosmid pKC644 in 10 μl of TE buffer were added to 75 μl of H$_2$O, 10 μl of 10X EcoRI buffer (1M Tris-HCl, pH=7.5; 0.5M NaCl; and 50 mM MgCl$_2$), and 5 μl (~100 units) of restriction enzyme EcoRI. The resulting reaction was incubated at 37° C. for 2 hours. The reaction mixture was extracted and the DNA was collected as described above. The DNA pellet was dissolved in ~10 μl of TE buffer. The DNA was electrophoresed on a low-melting agarose gel (BioRad, 2200 Wright Ave., Richmond, Ga., 94804) in substantial accordance with the procedure in Maniatis et al., 1982, Molecular Cloning (Cold Spring Harbor Laboratory).

The gel was prepared by heating 100 ml of 0.8% low-melting agarose in 1X TAE buffer (40 mM Tris-acetate, pH=7.5, 2 mM EDTA). The mixture was cooled to 37° C. and poured at 4° C. Two μl of loading-buffer (0.25% bromphenol blue, 0.25% xylene cyanol, 30% glycerol in H$_2$O) were added to the DNA sample. The sample was loaded onto the gel. The gel was run at 100 V at 4° C. until the bromphenol blue dye neared the bottom of the gel. The gel was stained with 0.5 μg/ml ethidium bromide and the desired ~10 kb EcoRI band was detected by long wave UV fluorescence and excised. To the gel piece was added 5 volumes of 20 mM Tris-HCl (pH 8.0) and 1 mM EDTA. The gel was melted at 65° C. for 5 minutes. The sample was extracted with an equal volume of phenol. The sample was centrifuged, the aqueous layer recovered and reextracted, and the DNA was collected as described above.

The DNA pellet was dissolved in 40 μl of TE buffer and contained ~2 μg of the desired ~10 kb EcoRI restriction fragment of cosmid pKC644.

The EcoRI-digested, dephosphorylated plasmid pHJL401 DNA (1 μl) was added to 10 μl (~0.5 μg) of the EcoRI restriction fragment from pKC644, 2 μl of 10X ligase buffer (660 mM Tris-HCl, pH=8; 66 mM MgCl$_2$; 10 mM dithiothreitol (DTT); and 10 mM ATP), and 6 μl of H$_2$O. About 1 μl (~100 units) of T4 DNA ligase was added to the solution of DNA, and the resulting reaction was incubated at 15° C. overnight (~16 hours). The ligated DNA contained the desired plasmid pKC668 and pKC668A which differ only in the orientation of the ~10 kb EcoRI insert fragment; a restriction site map of the insert DNA of pKC668 is presented in FIG. 2 of the accompanying drawings. A restriction map of the entire plasmid pKC668 is presented in FIG. 7.

The EcoRI site on plasmid pHJL401 resides within a polylinker that itself forms part of the DNA sequence encoding the lacZ α-fragment. Expression of the lacZ α-fragment in an *E. coli* ΔM15 strain, such as *E. coli* K12 DH5α, restores the strain's ability to produce a functional β-galactosidase enzyme. Thus, plasmid pHJL401 can restore β-galactosidase activity to the *E. coli* K12 DH5α strain. However, insertion of DNA into a restriction site of the polylinker on plasmid pHJL401, as occurs in the construction of plasmid pKC668, disrupts the lacZ α-fragment coding sequence and concomitantly destroys the ability of the plasmid pHJL401 derivative to complement the ΔM15 mutation. β-galactosidase can hydrolyze X-Gal, which is 5-bromo-4-chloro-3-indolyl-β-D-galactopyranoside, a colorless compound, to an indigo-colored product and thus allows for a convenient screening method for discriminating between transformants containing starting plasmid pHJL401 and those containing a plasmid pHJL401 derivative, such as plasmid pKC668.

Frozen competent DH5α cells (Bethesda Research Laboratories, Inc. (BRL), P.O. Box 6009, Gaithersburg, Md., 20877) were transformed as per manufacturer's instructions. The cells were thawed on ice, 100 μl of cells were removed per transformation, and the unused cells were refrozen in a dry ice-ethanol bath. The 100 μl of cells were added to 1 μl of the ligation reaction which had been diluted 5 fold with water. The cells were incubated on ice for 30 minutes, heat shocked at 42° C. for 2 minutes, and returned to ice for 2–5 minutes. One ml of SOC medium was added and the cells were incubated for one hour at 37° C. with shaking. SOC medium is 2% (w/v) tryptone, 0.5% (w/v) yeast extract, 20 mM glucose, 10 mM NaCl, 2.5 mM KCl, 10 mM MgCl$_2$, and 10 mM MgSO$_4$.

Aliquots of the transformation mixture were plated on L-agar plates containing 100 μg ampicillin/ml, 40 μg X-gal/ml, and 40 μg IPTG/ml. IPTG serves to derepress the lac promoter present on plasmid pHJL401. The plates were incubated at 37° C. overnight. Colonies that contain a plasmid without an insert, such as *E. coli* K12 DH5α/pHJL401, appear blue on these plates. Colonies that contain a plasmid with an insert, such as *E. coli* K12 DH5α/pKC668, are white. Several ampicillin-resistant, white colonies were selected and then screened by restriction enzyme analysis of their plasmid DNA. Plasmid DNA was obtained from the *E. coli* K12 DH5α/pKC668 transformants in accordance with the procedure for isolating plasmid pKC644 DNA, described above, except that the cells were grown at 37° C. rather than 30° C. and were grown in broth containing 100 μg/ml ampicillin rather than apramycin. The plasmid pKC668 DNA can be used to transform *Streptomyces fradiae* GS14 (NRRL 12188), *S. fradiae* GS50 (NRRL 12201), and the *S. fradiae* PM73 mutant strain, as described in Example 7, below.

EXAMPLE 3

Construction of Plasmid pKC604

A. Isolation of Vector Plasmid pOJ160

Plasmid pOJ160 (FIG. 6) can be obtained from the NRRL in *E. coli* K12 JM109 under the accession number NRRL B-18088. Plasmid pOJ160 is a useful vector because it can replicate in *E. coli* or Streptomyces and it has two selectable antibiotic resistance markers, apramycin and thiostrepton. Thiostrepton is selectable only in Streptomyces but apramycin is selectable in *E. coli* and Streptomyces. Plasmid pOJ160 also comprises a multiple cloning site in the lacZ gene which allows for the selection of DNA inserts by picking white transformants when plated on Xgal (See Example 2B). Plasmid DNA was obtained from the cells for use in the construction of plasmid pKC604 in substantial accordance with the procedure set forth in Example 1, above. A restriction site and function map of plasmid pOJ160 is presented in FIG. 6 of the accompanying drawings.

B. Final Construction of Plasmid pKC604

Plasmid pKC604 is an illustrative vector that comprises the srmG gene. Plasmid pKC604 was constructed in substantial accordance with the procedure set forth in Example 2B except that plasmid pOJ160 digested with restriction enzyme PstI was used as the vector rather than EcoRI-digested pHJL401 and an ~9 kb PstI fragment of cosmid pKC644 was used as the insert DNA rather than the ~10 kb EcoRI fragment of pKC644. Two plasmids, pKC604 and pKC604A, differing only in the orientation of the ~9 kb PstI fragment, were the result of this ligation. A restriction map of pKC604 is presented in FIG. 8.

EXAMPLE 4

Construction of Plasmid pKC1005

Plasmid pKC1005 is an illustrative vector that comprises the srmF gene. This srmF-comprising plasmid can be constructed in substantial accordance with the procedure of Example 2B except that the vector fragment is partially SalI-digested plasmid pOJ160 such that the resulting fragment is unit length and the insert DNA is an ~5.5 kb XhoI fragment of cosmid pKC644 (FIG. 2). XhoI ends are compatible with SalI ends. Two plasmids, pKC1005 and pKC1005A, differing only in the orientation of the ~5.5 kb XhoI fragment, are the result of this ligation. A restriction map of pKC1005 is presented in FIG. 9.

EXAMPLE 5

Isolation of Cosmid pKC571

Cosmid pKC571 is an illustrative vector that comprises the srmH gene. The cosmid pKC571 is available in *E. coli* SF8 from the NRRL under accession number NRRL B-18238. Cosmid pKC571 can be isolated in substantial accordance with the procedure set forth in Example 1. A restriction map of pKC571 is presented in FIG. 10.

EXAMPLE 6

Transformation of *Streptomyces ambofaciens* (NRRL 15263), *S. fradiae* GS14 (tylA mutant strain), *S. fradiae* GS50 (tylB mutant strain), and *S. fradiae* PM73 (tylB mutant strain)

A. List of Solutions

The following solutions are referred to throughout the Examples and are presented here for clarity.

| Ingredient | Amount |
| --- | --- |
| 1. P Medium (~100 ml): | |
| Sucrose | 10.3 g |
| $K_2SO_4$ | 0.025 g |
| Trace element solution (see #3) | 0.2 ml |
| $MgCl_2.6H_2O$ | 0.203 g |
| Water | 80 ml |
| After autoclaving add: | |
| $KH_2PO_4$ (0.5%) | 1 ml |
| $CaCl_2.2H_2O$ (3.68%) | 10 ml |
| (N-tris-(hydroxymethyl)-methyl-2-aminoethane sulphonic acid), "TES" buffer, 0.25 M, pH = 7.2 | 10 ml |
| 2. Trace element solution (~1 L): | |
| $ZnCl_2$ | 40 mg |
| $FeCl_3.6H_2O$ | 200 mg |
| $CuCl_2.2H_2O$ | 10 mg |
| $MnCl_2.4H_2O$ | 10 mg |
| $Na_2B_4O_7.10H_2O$ | 10 mg |
| $(NH_4)_6Mo_7O_{24}.4H_2O$ | 10 mg |
| $H_2O$ | 1 L |
| 3. R2 Regeneration Medium (~1 L): | |
| Sucrose | 103 g |
| $K_2SO_4$ | 0.25 g |
| Trace element solution | 2 ml |
| $MgCl_2.6H_2O$ | 10.12 g |
| glucose | 10 g |
| L-asparagine.$1H_2O$ | 2.0 g |
| casamino acids | 0.1 g |
| Agar | 22 g |
| Water | to 700 ml |
| The pH is adjusted to pH = 7.2 before autoclaving. | |
| After autoclaving, add: | |
| $KH_2PO_4$ (0.05 g/100 ml) | 100 ml |
| $CaCl_2$ (2.22 g/100 ml) | 100 ml |
| TES Buffer (5.73 g/100 ml, pH = 7.2) | 100 ml |
| 4. Soft Nutrient Agar (SNA, ~1 L): | |
| Difco Bacto Nutrient Broth | 8 g |
| Agar | 5 g |
| 5. R2YE medium is R2 medium with 20 ml of 25% yeast extract added per liter. | |
| 6. Yeast Extract - Malt Extract (YEME, ~1 L): | |
| Yeast extract | 3 g |
| Peptone | 5 g |
| Malt extract | 3 g |
| Glucose | 10 g |
| 7. YEME + 34% Sucrose Liquid Complete Media is YEME with 340 g/L of sucrose. | |
| 8. YMX Medium (~1 L): | |
| Yeast extract | 3 g |
| Malt extract | 3 g |
| Glucose | 2 g |
| Agar | 20 g |
| 9. YMX Agar is 0.3% yeast extract, 0.3% malt extract, dextrose, and 2.0% agar. | |
| 10. Tylosin Fermentation Medium | |
| Beet Molasses | 2% |

-continued

| Ingredient | Amount |
| --- | --- |
| Corn Meal | 1.5% |
| Fish Meal | 0.9% |
| Corn Gluten | 0.9% |
| Sodium Chloride | 0.1% |
| Ammonium Phosphate (dibasic) | 0.04% |
| Calcium Carbonate | 0.2% |
| Crude Soybean Oil | 3% |
| The pH of this medium was adjusted to 7.1 with 1 N NaOH. | |
| 11. AS1 Medium (~1 L deionized H$_2$O) | |
| Yeast Extract | 1 g |
| L-alanine | 0.2 g |
| L-arginine (free base) | 0.2 g |
| L-asparagine | 0.5 g |
| Soluble Starch | 5 g |
| Sodium Chloride | 2.5 g |
| Sodium Sulfate | 10 g |
| Meer Agar | 20 g |
| 12. Spiramycin Fermentation Medium (~1 L) | |
| Yeast Extract | 10 g |
| KCl | 2.5 g |
| MgSO$_4$ | 0.1 g |
| KH$_2$PO$_4$ | 10 g |
| FeCl$_2$ | 0.03 g |
| ZnCl$_2$ | 0.03 g |
| MnCl$_2$ | 0.01 g |
| Ammonium Molybdate | 0.005 g |

These ingredients were dissolved in 800 ml of water and autoclaved. To this was added sterile potato dextrin (15 g) and glucose (10 g) in 200 ml of water.

B. Transformation of Streptomyces

Five ml of a fully grown overnight culture of Streptomyces, homogenized and sonicated, were used to inoculate 20 ml of TSB plus 0.3% glycine. The culture was incubated at 30° C. for 24 hours. After homogenization with a tissue grinder, 5 ml of homogenate was used to inoculate 20 ml of fresh TSB supplemented with 0.3% glycine. The culture was incubated at 30° C. for 24 hours. The culture was homogenized and transferred to a 50 ml sterile polystyrene centrifuge tube. The cells were pelleted by centrifugation for 10 minutes at 3500 rpm, washed with 10 ml of P medium and re-pelleted. The cells were then resuspended in 15-20 ml of P medium with 1 mg/ml lysozyme and incubated at room temperature for 1.5 hours. Protoplast formation was monitored by examining small samples under a phase-contrast microscope. Protoplasts are spherical.

The protoplasts were centrifuged as before and washed twice in P medium. The cells were resuspended in 20 ml of P medium and 200 μl of protoplasts for each transformation were placed in a 1.5 ml Eppendorf® tube. Up to 10 μl of DNA solution were added with gentle mixing. Nine hundred μl of 50% polyethylene glycol 1000 in P medium were added immediately. One half ml of transformation mix in 4 ml of modified R2 top agar was poured onto dried modified R2 plates. The plates were incubated at 30° C. for 24 hours. The plates were then overlaid with modified R2 top agar containing an appropriate amount of the desired antibiotic. With pHJL401-derived plasmids, thiostrepton was used at 50 μg/ml. With pOJ160 or pKC473 derived plasmids, apramycin was used at 50 μg/ml. When the Tn5 NmR gene was present, neomycin was used at 10 ||g/ml. The plates were incubated at 30° C. and transformants appeared 2-3 days later (7-10 days with S. fradiae). The transformants were analyzed for the presence of appropriate plasmid DNA by the method of Example 7, set out below.

EXAMPLE 7

Rapid Isolation of Plasmid DNA from Streptomyces

The cells were grown in 25 ml of TSB supplemented with a suitable concentration of the appropriate antibiotic as explained in Example 6B. The cells were washed once in 10.3% sucrose, pelleted, and resuspended in 5 ml of lysozyme solution (5 mg/ml lysozyme in 0.3M sucrose, 25 mM Tris.HCl, pH 8.0, 25 mM EDTA). The mixture was incubated for 30 minutes at room temperature and 22.5 ml of alkaline lysis solution (0.3M sodium hydroxide and 1% SDS) was added. Immediately, the solution was vortexed vigorously, then incubated at 50° C. for 30 minutes. The solution was then vortexed vigorously, then two ml of acid phenol:Sevag (chloroform-:isoamyl alcohol, 24:1) were added, and the extraction was vortexed vigorously again. The layers were separated by centrifugation in a table top centrifuge. The aqueous layer (~7 ml) was transferred into a tube containing 0.7 ml of 3M sodium acetate. An equal volume of 2-propanol was added and the mixture vortexed. Incubation was carried out for 10 minutes at room temperature. The DNA was pelleted by centrifugation for 10 minutes at 10,000 rpm. The liquid was decanted, centrifuged for 20 seconds, and the last traces of liquid removed with tissue paper.

The pellet was dissolved in 0.5 ml of TE buffer and transferred to an Eppendorf® tube containing 50 μl of 3M sodium acetate. The solution was extracted once with neutral phenol:Sevag, once with Sevag and then precipitated with an equal volume of 2-propanol. The mixture was centrifuged for 2 minutes and all of the liquid was removed as before. The pellet was redissolved in 0.5 ml of TE buffer and 5 μl of 0.5M spermine.HCl was added. The solution was mixed, incubated at room temperature for 5 minutes, and centrifuged for 5 minutes. The liquid was removed. The pellet was washed in 1 ml of a solution containing 70% ethanol, 0.3M sodium acetate and 10 mM magnesium acetate. The mixture was incubated for 5 minutes at room temperature and centrifuged for 5 minutes. The liquid was removed and the pellet dried. The pellet was redissolved in 25 μl of TE and 1-2 μl was used for each restriction enzyme digest.

EXAMPLE 8

Assay of Antibiotic Production by Streptomyces

A. Plate-Plug Assay

To determine whether a strain produced antibiotic, Streptomyces ambofaciens and S. fradiae transformants or mutant strains were patched from the R2-agar regeneration plates to AS1 plates containing a suitable concentration of the appropriate antibiotic and incubated at 30° C. for 2-3 days (5-7 days for S. fradiae) until the colonies were 5-10 millimeters in diameter. The colonies were then plugged with a sterile transfer tube (Spectrum Medical Industrial, Inc., Los Angeles, Calif. 90054) and transferred to trypticase soy agar (TSA) plates, which had been previously overlayed with soft-agar nutrient broth (Difco Laboratories, Detroit, Mich. 48232) containing Micrococcus luteus X160 (ATCC 9341). The plates were incubated at 37° C. for 16-24 hours. Micrococcus luteus is sensitive to tylosin and spiramycin and resistant to apramycin. Consequently, this *M. luteus* strain cannot grow around a plug which contains Streptomyces that are producing tylosin or spiramycin. A zone of inhibition indicates the presence of antibiotic.

B. Bioautography

The agar from an entire plate containing the organism of interest which has been grown for the appropriate time at 30° C. was macerated in 10 ml of 1M Tris-HCl pH 8.0 in a 50 ml polypropylene centrifuge tube. Ten ml of ethyl acetate were added and the mixture was shaken vigorously several times over a period of 1-2 hours at room temperature. The layers were separated in a tabletop centrifuge and the top ethyl acetate layer was recovered and evaporated to dryness in a dish. The residue was dissolved in 1 ml of methanol. Approximately 1-20 $\mu$l of the methanol extract were applied to a TLC plate and dried. Separation was carried out on a thinlayer chromatography plate (Merck, P.O. Box 2000, Rahway, N.J. 07065, pre-coated silica gel #60 F-254) next to a tylosin or spiramycin standard. When agar plugs were being assayed, the plugs were left on the plate for a time sufficient for diffusion to occur; then, the plate was subjected to ascending liquid chromatography in 95:5:5 ethylacetate:diethylamine:methanol. The developed chromatograms were dried thoroughly in a fume hood for at least two hours. The chromatograms were then placed face down on *Micrococcus luteus* X160-seeded TSA plates for ~15 minutes. The chromatograms were removed from the plates, and the plates were incubated at 37° for 16-24 hours. Zones of inhibition were compared with a tylosin or spiramycin standard.

C. Fermentation

Cultures were grown on slants of AS1 medium containing a suitable amount of the appropriate antibiotic as explained in Example 6B. These cultures were individually used to inoculate several 50 ml aliquots of AS1 medium, or tylosin or spiramycin fermentation media. Methanol extracts of the media were analyzed by TLC substantially in accordance with Example 8B.

EXAMPLE 9

Generation of Spiramycin Mutant Strains

A. Mutagenesis in vitro of Cosmid pKC644 insert DNA

Cosmid pKC644 (AmR) was isolated in accordance with the procedure of Example 1. Two samples of about 10 $\mu$g each (in 10 $\mu$l TE) were digested with the restriction enzymes BamHI and SalI respectively. The enzymes were used to generate partial digestions in accordance with Maniatis et al., pp. 282-285, 1982, *Molecular Cloning* (Cold Springs Harbor Laboratory), herein incorporated by reference. The conditions were adjusted such that the end-products were unit length molecules. The restriction cuts of each molecule were at any one of the many SalI or BamHI restriction sites present in the pKC644 insert DNA. The sample pools represented a variety of said cuts. The SalI and BamHI digested DNA's were dephosphorylated in accordance with Example 2B. A NmR and BlR fragment from the pKIXX plasmid (Pharmacia, 800 Centennial Ave., Piscataway, N.J., 08854) with BamHI or XhoI (SalI compatible) ends was isolated by digesting the pKIXX plasmid with the two enzymes separately. Each fragment was ligated to the pool of digested pKC644 with compatible ends (BamHI→BamHI, XhoI→SalI) in accordance with Example 2B. The ligation was packaged in vitro using Gigapack® from Stratagene (11099 N. Torrey Pines Rd., LaJolla, Calif. 92037) under conditions specified by the manufacturer.

Phage transduction was carried out by initially growing a 10 ml culture of *E. coli* BE 1879 overnight in TY broth (per liter:10 g tryptone, 5 g yeast extract, 10 g sodium chloride) supplemented with 0.2% maltose. The cells were centrifuged at 2000 rpm for 10 minutes and resuspended in one-half volume 10 mM MgSO$_4$. Various dilutions of phage in 10 mM Tris.HCl pH 7.5, 10 mM MgSO$_4$ were incubated with 200 $\mu$l of cells at 37° C. for 20 minutes. The mixture was diluted to 1 ml with TY broth and the cells were grown for 2 hours at 30° C. The cells were added to 3 ml TY soft agar (0.5% agar) kept at 48° C. and plated onto TY plates supplemented with 5 $\mu$g/ml bleomycin and 100 $\mu$g/ml apramycin. The plates were incubated overnight at 30° C.

B. Rapid Isolation of Plasmid DNA from *E. coli*

Several transductants were picked to analyze their plasmid DNA to confirm insertions into the cloned *Streptomyces ambofaciens* DNA. Five ml cultures were grown at 30° C. overnight in TY broth supplemented with apramycin at 100 $\mu$g/ml. The cells from 4 ml of each overnight culture were pelleted in a table top centrifuge. The supernatant was decanted and the cell pellet resuspended in 0.5 ml of 25 mM Tris.HCl, pH 8.0, 25 mM EDTA. Then the solution was transferred to a 1.5 ml microfuge tube. To this solution was added 250 $\mu$l of 0.3N NaOH, 2% SDS, and the mixture vortexed thoroughly. The mixture was incubated at 70° C. for 10 minutes, then cooled to room temperature. One hundred $\mu$l of acid phenol:Sevag were added and vortexed immediately, then centrifuged for 2 minutes in a microfuge. The top layer was removed and transferred to a fresh tube. Seventy $\mu$l of 3M sodium acetate were added and the tube filled with 2-propanol, then mixed well by vortexing. The solution was incubated for 5 minutes at room temperature. Centrifugation was carried out for 5 minutes in a microfuge and the supernatant removed. The pellet was centrifuged briefly and the remaining liquid removed.

The pellet was dissolved in 500 $\mu$l of TE buffer. To the DNA solution 5 $\mu$l of 500 mM spermine.HCl (5 mM final concentration; spermine stock solution is stored at −20° C.) was added. The solution was mixed and incubated at room temperature for 5 minutes, then centrifuged for 5 minutes. The supernatant was removed and the pellet resuspended in 300 $\mu$l of 0.3M sodium acetate and 0.01M MgCl$_2$. Seven hundred $\mu$l of cold ethanol were added, vortexed, and incubated for 5 minutes at room temperature. The DNA-containing solution was centrifuged for 5 minutes, the supernatant removed and the pellet washed with 100% ethanol and dried. The DNA pellet was dissolved in 10 $\mu$l of TE and 0.2-1 $\mu$l used for restriction enzyme analysis. Plasmid DNAs that were demonstrated to contain inserts were pooled. Pooled plasmid DNA was prepared in the manner set out above from transductants generated from BamHI or SalI ligations.

EXAMPLE 10

Mutagenesis in vivo of cosmid pKC644 insert DNA

A. Preparation of pKC644 Lysates

The cosmid pKC644 (AmR) was introduced into the Tn10 hopping strain *E. coli* K12 BE1997, deposited with the NRRL under accession number B-18372. The hopping strain includes: (i) a Tn10 element (Elt 12) comprising the Tn5 NmR and BlR genes on an F' element; (ii) a transposase gene (Elt 13) on a TcR pACYC184 plasmid that is compatible with pBR322 origins, and (iii) a defective λ cI857 prophage that can package cosmid pKC644 upon heat induction at 42° C.

The *E. coli* strain BE1989 which comprises the cosmid pKC644 (NRRL B-18238), was inoculated into 250 ml of TY broth supplemented with 100 μg/ml apramycin. The culture was kept at 30° C. overnight with no shaking. Two hundred fifty μl of 2M MgSO$_4$ were added and the flask heated by flame to 42° C. for 15 minutes. After this induction, the flask was incubated at 37° C. with shaking for 5 hours. The cells were centrifuged and resuspended in 5 ml of 10 mM Tris.HCl pH 7.5, 10 mM MgSO$_4$. The cells were then taken through three cycles of freezing in a dry ice-ethanol bath and thawing in a 37° C. water bath to promote lysis. Ten μl of DNase I (10 mg/ml) were added and the mixture incubated at 37° C. for 10 minutes, then centrifuged at 10,000 rpm for 10 minutes. The supernatant (∼2.5 ml) was recovered, 250 μl of chloroform were added, and the lysate stored at 4° C. until use.

B. Tn10 mutagenesis of cosmid pKC644

BE1997 (Tn10 hopping strain) was grown overnight at 30° C. in TY broth supplemented with 0.2% maltose and 10 mM MgSO$_4$ (TYMM). Five ml of the culture were inoculated into 20 ml of TYMM supplemented with 12.5 μg/ml tetracycline and 25 μg/ml neomycin in a 250 ml flask. The culture was incubated at 30° C. for 1 hour with shaking. The cells were centrifuged and resuspended in 1 ml of 10 mM Tris.HCl, pH=7.5, 10 mM MgSO$_4$. Five hundred μl of cells were mixed with 100 μl of the pKC644 lysate generated in Example 11A. This was incubated at 30° C. for 10 minutes with no shaking. To the culture was added 2.5 ml of TY broth. The mixture was placed on a rotating wheel at 30° C. for 1 hour. Three ml were transferred to 50 ml TY supplemented with 100 μg/ml apramycin, 12.5 μg/ml tetracycline, and 5 μg/ml bleomycin in a 250 ml flask. This was incubated at 30° C. for 1.5 hours. To induce the expression of the transposase gene under the control of the tac promoter, 50 μl of 20M MgCl$_2$ and 50 μl of 1M IPTG were added and incubation was continued at 30° C. for 1 hour. The transposase gene causes the Tn10 transposon carrying the NmR and BlR genes to be randomly transposed into the chromosome and the extrachromosomal elements, including desired insertions into pKC644 insert DNA. Packaging of the cosmid was then induced by heat treatment at 42° C. for 15 minutes, which inactivates the lambda repressor. During the subsequent incubation at 37° C. for 3 hours, phage particles accumulate but the cells do not lyse because the prophage is defective for lysis. The cells were then centrifuged and resuspended in 3 ml of 10 mM Tris.HCl, pH=7.5, 10 mM MgSO$_4$. Three freeze-thaw cycles were carried out in a dry ice-ethanol bath and a 37° C. water bath. Two and one-half μl of DNase I (10 mg/ml) were added. The mixture was incubated at 37° C. for 10 minutes. Chloroform (100 μl) was then added, the mixture vortexed, and the cell debris centrifuged out. The mutant lysate supernatant was recovered and 50 μl of chloroform was added. The lysate was stored at 4° C. until use.

C. Infection of *E. coli* BE 1879 by Mutated Lysate of Cosmid pKC644

The infection was carried out in substantial accordance with Example 10A. One hundred μl of the infected cells were plated onto TY agar plates containing 100 μg/ml apramycin and 5 μg/ml bleomycin. Several hundred colonies were obtained. Plasmid DNA from these transductants was analyzed to identify insertions into the cloned *Streptomyces ambofaciens* DNA of pKC644 in accordance with the method of Example 10. A number of transformants were identified that contained plasmids with the desired inserts.

EXAMPLE 12

Introduction of Mutations Generated In Vivo and In Vitro into the *Streptomyces ambofaciens* Genome Transformation of Mutant Cosmids into *Streptomyces ambofaciens*

Mutant cosmid DNAs generated in vitro (BamHI pool and SalI pool) and in vivo (via the Tn10 hopping strain) were introduced into *Streptomyces ambofaciens* protoplasts substantially in accordance with Example 6, except that the transformants were plated onto R2YE medium supplemented with 10 μg/ml neomycin. NmR transformants were tested for sensitivity to apramycin, indicating that a double cross-over of the mutated insert DNA into the chromosome had occurred. These transformants were tested for the production of spiramycin in substantial accordance with the teachings of Example 8.

EXAMPLE 12

Characterization of Spiramycin Biosynthetic Gene Mutants

A. Co-Fermentation with other Mutants

Strains that were found not to produce spiramycin when analyzed by the procedure of Example 11 were streaked onto AS1 plates. Each mutant was crossed against every other mutant. The streaks were done perpendicularly. The plates were incubated for 4 days at 30° C. Plugs of agar were removed at the point of intersection of two strains, and the co-fermenting pairs were analyzed for the production of spiramycin by the method of Example 8. The results are given in Table III, below.

TABLE III

| Mutant Pair | Spiramycin Produced |
|---|---|
| srm-7, srm-8 | no |
| srm-7, srm-12 | no |
| srm-7, srm-14 | no |
| srm-7, srm-22 | no |
| srm-8, srm-12 | no |
| srm-8, srm-14 | no |
| srm-8, srm-22 | no |
| srm-12, srm-14 | yes |
| srm-12, srm-22 | yes |
| srm-14, srm-22 | no |

B. Response to Tylactone Supplementation

The mutants were tested for the production of an antibiotic when grown for 5 days on AS1 plates supplemented with 0.1 mM tylactone. The mutants were grown for 5 days at 30° C., then tested for the production of an antibiotic by the method of Example 8. The results are shown in Table IV.

TABLE IV

| Mutant Strain | Response | Antibiotic Produced |
|---|---|---|
| srm-7 | no | none |
| srm-8 | no | none |
| srm-12 | no | none |
| srm-14 | yes | yes |
| srm-22 | yes | yes |

As a result of the experiments set out in this Example, the mutations were shown to reside in three genes. Srm-12 carries a mutation in the srmF gene. The srm-7 and srm-8 mutant strains represent two separate mutations in the srmG gene. The srmH gene is also represented by the mutations in two separate mutant strains, srm-14 and srm-22. The mutations were mapped by Southern hybridization and restriction analysis as described in Maniatas et al., supra. The map positions of the mutations are shown in FIG. 2.

Although specific mutants are presented here, one skilled in the art will recognize that the procedures described above are capable of producing other strains containing mutant genes which will function analogously to those presented in this Example. Consequently, the preparation of mutant gene-containing strains is not to be constituted as limited to the specific mutants prepared here.

We claim:

1. A recombinant DNA sequence comprising a spiramycin antibiotic biosynthetic gene wherein said antibiotic biosynthetic gene is selected from the group consisting of the srmD, srmE, srmF, and srmH spiramycin antibiotic biosynthetic genes of *Streptomyces ambofaciens*.

2. The DNA sequence of claim 1 wherein said gene is srmD.

3. The DNA sequence of claim 1 wherein said gene is srmE.

4. The DNA sequence of claim 1 wherein said gene is srmF.

5. The DNA sequence of claim 1 wherein said gene is srmH.

6. The DNA sequence of claim 1 that is a recombinant DNA vector.

7. The vector of claim 6 that is a plasmid.

8. The vector of claim 7 that is cosmid pKC644.

9. The vector of claim 7 that is plasmid pKC668.

10. The vector of claim 7 that is plasmid pKC668A.

11. The vector of claim 7 that is plasmid pKC604A.

12. The vector of claim 7 that is plasmid pKC1005.

13. The vector of claim 7 that is plasmid pKC1005A.

14. The vector of claim 7 that is cosmid pKC571.

15. A recombinant DNA host cell transformed with the vector of claim 6.

16. The host cell of claim 15 that is Streptomyces.

17. The host cell of claim 15 that is *Streptomyces ambofaciens*.

18. The host cell of claim 15 that is *Streptomyces fradiae*.

19. The host cell of claim 17 that is *Streptomyces ambofaciens*/pKC644.

20. The host cell of claim 17 that is *Streptomyces ambofaciens*/pKC668.

21. The host cell of claim 17 that is *Streptomyces ambofaciens*/pKC1005.

22. The host cell of claim 17 that is *Streptomyces ambofaciens*/pKC571.

23. The host cell of claim 18 that is *Streptomyces fradiae*/pKC644.

24. The host cell of claim 18 that is *Streptomyces fradiae*/pKC668.

25. The host cell of claim 18 that is *Streptomyces fradiae*/pKC1005.

26. The host cell of claim 18 that is *Streptomyces fradiae*/pKC571.

27. A method of generating a *Streptomyces ambofaciens* host cell containing an inactivated antibiotic biosynthetic gene where said method comprises:
   (1) changing the nucleotide sequence of a spiramycin biosynthetic gene, wherein said gene is selected from the group consisting of the srmD, srmE, srmF, and srmH spiramycin antibiotic biosynthetic genes of *Streptomyces ambofaciens*, by recombinant DNA methodology;
   (2) transforming said gene of step (1) into an antibiotic-producing *Streptomyces ambofaciens* host cell; and
   (3) identifying the transformed cells of step (2) that have incorporated the inactivated gene of step (1) through a process of homologous recombination.

28. The method of claim 27 wherein said gene is srmD.

29. The method of claim 27 wherein said gene is srmE.

30. The method of claim 27 wherein said gene is srmF.

31. The method of claim 27 wherein said gene is srmH.

32. The *Streptomyces ambofaciens* host cell generated by the method of claim 27.

33. The host cell of claim 32 that is *Streptomyces ambofaciens* srm-14.

34. The host cell of claim 32 that is *Streptomyces ambofaciens* srm-22.

35. The host cell of claim 32 that is *Streptomyces ambofaciens* srm-12.

36. A *Streptomyces ambofaciens* host cell that comprises an inactivated antibiotic biosynthetic gene where said host cell is generated by:
   (1) changing the nucleotide sequence of a spiramycin biosynthetic gene, wherein said spiramycin antibiotic biosynthetic gene is selected from the group consisting of the srmD, srmE, srmF, and srmH spiramycin antibiotic biosynthetic genes of *Streptomyces ambofaciens*, by recombinant DNA methodology;
   (2) transforming said gene of step (1) into an antibiotic-producing *Streptomyces ambofaciens* host cell; and
   (3) identifying the transformed cells of step (2) that have incorporated the inactivated gene of step (1) through a process of homologous recombination.

37. The host cell of claim 36 wherein said gene is srmD.

38. The host cell of claim 36 wherein said gene is srmE.

39. The host cell of claim 36 wherein said gene is srmF.

40. The host cell of claim 36 wherein said gene is srmH.

41. The host cell of claim 36 that is *Streptomyces ambofaciens* srm-12.

42. The host cell of claim 36 that is *Streptomyces ambofaciens* srm-14.

43. The host cell of claim 36 that is *Streptomyces ambofaciens* srm-22.

* * * * *